US006896874B2

(12) United States Patent
Li et al.

(10) Patent No.: US 6,896,874 B2
(45) Date of Patent: May 24, 2005

(54) MR-SIGNAL EMITTING COATINGS

(75) Inventors: Junwei Li, Madison, WI (US); Orhan Unal, Madison, WI (US); Xiqun Jiang, Nanjing (CN); Charles Milton Strother, Madison, WI (US); Hyuk Yu, Blue Mounds, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/142,363

(22) Filed: May 9, 2002

(65) Prior Publication Data

US 2003/0099764 A1 May 29, 2003

Related U.S. Application Data

(63) Continuation-in-part of application No. 10/096,368, filed on Mar. 12, 2002, which is a continuation of application No. 09/105,033, filed on Jun. 25, 1998, now Pat. No. 6,361,759
(60) Provisional application No. 60/086,817, filed on May 26, 1998.

(51) Int. Cl.$^7$ .............................................. A61B 5/055
(52) U.S. Cl. ..................... 424/9.323; 424/9.1; 424/9.3; 424/9.32; 424/9.36
(58) Field of Search ................................ 424/9.3, 9.32, 424/9.322, 9.323, 9.36, 9.1; 600/8, 410, 411, 415; 128/654, 653.2

(56) References Cited

U.S. PATENT DOCUMENTS

| | | | |
|---|---|---|---|
| 4,855,353 A | 8/1989 | Kurami | |
| 4,986,980 A | 1/1991 | Jacobsen | |
| 5,039,512 A | 8/1991 | Kraft et al. | |
| 5,087,440 A | 2/1992 | Cacheris et al. | |
| 5,098,692 A | 3/1992 | Gries et al. | |
| 5,264,634 A | 11/1993 | Becker et al. | |
| 5,583,206 A | 12/1996 | Snow et al. | |
| 5,627,079 A | 5/1997 | Gardella, Jr. et al. | |
| 5,744,958 A | 4/1998 | Werne | |
| 5,817,292 A | 10/1998 | Snow et al. | |
| 5,932,188 A | 8/1999 | Snow et al. | |
| 5,980,862 A * | 11/1999 | Meade et al. | 424/9.35 |
| 6,361,579 B1 | 3/2002 | Itoh et al. | |
| 6,395,299 B1 * | 5/2002 | Babich et al. | 424/484 |
| 2003/0077225 A1 | 4/2003 | Laurent et al. | |

FOREIGN PATENT DOCUMENTS

| | | |
|---|---|---|
| EP | 0 331 616 A2 | 9/1989 |
| WO | WO 92/00748 | 1/1992 |
| WO | WO 94/08629 | 4/1994 |
| WO | WO 94/23782 | 10/1994 |
| WO | WO 95/05669 | 2/1995 |
| WO | WO 95/24225 | 9/1995 |
| WO | WO 96/00588 | 1/1996 |
| WO | WO 98/28258 | 7/1998 |
| WO | WO 99/60920 | 12/1999 |
| WO | WO 01/81460 | 11/2001 |
| WO | WO 02/22186 | 3/2002 |

OTHER PUBLICATIONS

Xiqun Jiang, et al., "Novel Magnetic Resonance Signal Enhancing Coating Material," Advanced Materials, CHG Verlagsgesellschaff, Weinheim, DE, vol. 13, No. 7, Apr. 4, 2001 pp. 490–493.

Database Caplus, Chemical Abstracts Service, Columbus, Ohio, US, Kende, Andrew S., et al. "Synthesis of some novel functionalized double Michael acceptors based on bis (vinylsulfonyl) methane (BVSM)", retrieved from STN, Database accession No. 1996:721056, XPP002281329 abstract & Organic Preparations and Procedures International, 28(6), 683–690, Coden: Oppiak, ISSN: 0030–4948, 1996.

Ladd et al., Proc. ISMRM (1997) 1937.

F.R. Korosec, R. Frayne, T.M. Grist. C.A. Mistretta, 36 Magn. Reson. Medicine, (1996) 345–351.

Fried et al., Image Guided Surgery, Laryngoscope, vol. 106, No. 4, (1996) 411–417.

* cited by examiner

*Primary Examiner*—Dameron L. Jones
(74) *Attorney, Agent, or Firm*—Michael Best & Friedrich LLP

(57) ABSTRACT

The present invention provides a coating that emits magnetic resonance signals and a method for coating medical devices therewith. The coating includes a paramagnetic metal ion-containing polymer complex that facilitates diagnostic and therapeutic techniques by readily visualizing medical devices coated with the complex. The present invention also provides methods by which pre-existing polymers and medical devices may be made MR-imageable. The invention also provides methods of improving MR-imageability of polymers and medical devices by encapsulating the polymers and medical devices with hydrogels.

102 Claims, 22 Drawing Sheets

(1) -NH-CO-, amide linkage
(3) SurModics proprietary process, most likely photo-initiated.
(4) a. If hydrogel chain is poly(acrylamide), bisacrylamide is crosslinker

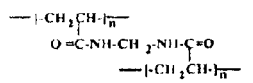

N, N'-methylene-bisacrylamide crosslinker b. If hydrogel chain is gelatin, glutaraldehyde is crosslinker,
-N=CH-CH2-CH2-CH2-CH=N-

(5) DTPA-Gd(III) complex

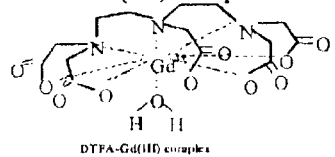

DTPA-Gd(III) complex (6) SurModics proprietary material (7) a. poly(acrylamide), b. gelatin

Figure 14

(1) -NH-CO-, amide linkage
(2) Hydrophobic patches of PE surfaces
(3) Hydrogel chain is gelatin, so glutaraldehyde is the crosslinker for both gelatin-gelatin and gelatin-primary polymer(amine containing),
(4) DTPA-Gd(III) complex    (5) poly(N-[3-aminopropyl]-methacrylamide)
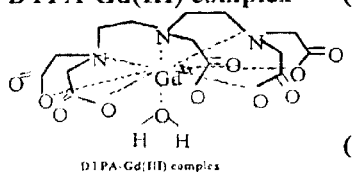
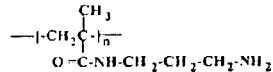
(6) gelatin
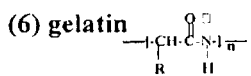
Figure 17

(1) -NH-CO-, amide linkage
(2) Hydrophobic patches on PE surfaces
(3) Hydrogel chain is gelatin, so glutaraldehyde is the crosslinker
(4) DTPA-Gd(III) complex    (5) gelatin
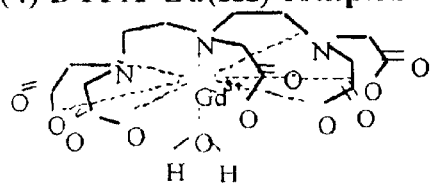
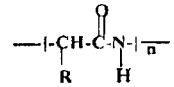
DTPA-Gd(III) complex
Figure 20

MR-SIGNAL EMITTING COATINGS

CROSS-REFERENCE TO RELATED APPLICATIONS

This application is a continuation-in-part of and claims priority to U.S. application Ser. No. 10/096,368 filed on Mar. 12, 2002 which is a continuation of and claims priority to U.S. application Ser. No. 09/105,033 which was filed on Jun. 25, 1998 and issued as U.S. Pat. No. 6,361,759 on Mar. 26, 2002 and claims the benefit of the priority date under 35 U.S.C. §119 of U.S. Provisional Application No. 60/086,817, filed May 26, 1998. This application claims priority to each of these applications and hereby fully incorporates the subject matter of each of these applications.

STATEMENT REGARDING FEDERALLY SPONSORED RESEARCH OR DEVELOPMENT

This invention was made with Government support under Grant Nos. NIH 1 ROI HL57983; NIH 1 R29 HL57501 awarded by the National Institutes of Health, and NSF-DMR 9711226, 0084301 and NSF-EEC 8721845(ERC) awarded by the National Science Foundation. The U.S. Government has certain rights in this invention.

BACKGROUND OF THE INVENTION

This invention relates in general to coatings that emit magnetic resonance signals and in particular, to such coatings containing paramagnetic metal ions, and to a process for coating devices and implants with such coatings so that these devices are readily visualized in magnetic resonance images during diagnostic or therapeutic procedures done in conjunction with magnetic resonance imaging (MRI).

Since its introduction, magnetic resonance (MR) has been used to a large extent solely for diagnostic applications. Recent advancements in magnetic resonance imaging now make it possible to replace many diagnostic examinations previously performed with x-ray imaging with MR techniques. For example, the accepted standard for diagnostic assessment of patients with vascular disease was, until quite recently, x-ray angiography. Today, MR angiographic techniques are increasingly being used for diagnostic evaluation of these patients. In some specific instances such as evaluation of patients suspected of having atheroscleroic disease of the carotid arteries, the quality of MR angiograms, particularly if they are done in conjunction with contrast-enhancement, reaches the diagnostic standards previously set by x-ray angiography.

More recently, advances in MR hardware and imaging sequences have begun to permit the use of MR for monitoring and control of certain therapeutic procedures. That is, certain therapeutic procedures or therapies are performed using MR imaging for monitoring and control. In such instances, the instruments, devices or agents used for the procedure and/or implanted during the procedure are visualized using MR rather than with x-ray fluoroscopy or angiography. The use of MR in this manner of image-guided therapy is often referred to as interventional magnetic resonance (interventional MR). These early applications have included monitoring ultrasound and laser ablations of tumors, guiding the placement of biopsy needles, and monitoring the operative removal of tumors.

Of particular interest is the potential of using interventional MR for the monitoring and control of endovascular therapy. Endovascular therapy refers to a general class of minimally-invasive interventional (or surgical) techniques which are used to treat a variety of diseases such as vascular disease and tumors. Unlike conventional open surgical techniques, endovascular therapies utilize the vascular system to access and treat the disease. For such a procedure, the vascular system is accessed by way of a peripheral artery or vein such as the common femoral vein or artery. Typically, a small incision is made in the groin and either the common femoral artery or vein is punctured. An access sheath is then inserted and through the sheath a catheter is introduced and advanced over a guide-wire to the area of interest. These maneuvers are monitored and controlled using x-ray fluoroscopy and angiography. Once the catheter is properly situated, the guide-wire is removed from the catheter lumen, and either a therapeutic device (e.g., balloon, stent, coil) is inserted with the appropriate delivery device, or an agent (e.g., embolizing agent, anti-vasospasm agent) is injected through the catheter. In either instance, the catheter functions as a conduit and ensures the accurate and localized delivery of the therapeutic device or agent to the region of interest. After the treatment is completed, its delivery system is withdrawn, i.e., the catheter is withdrawn, the sheath removed and the incision closed. The duration of an average endovascular procedure is about 3 hours, although difficult cases may take more than 8 hours. Traditionally, such procedures have been performed under x-ray fluoroscopic guidance.

Performing these procedures under MR-guidance provides a number of advantages. Safety issues are associated with the relatively large dosages of ionizing radiation required for x-ray fluoroscopy and angiographic guidance. While radiation risk to the patient is of somewhat less concern (since it is more than offset by the potential benefit of the procedure), exposure to the interventional staff can be a major problem. In addition, the adverse reactions associated with MR contrast agents is considerably less than that associated with the iodinated contrast agents used for x-ray guided procedures.

Other advantages of MR-guided procedures include the ability to acquire three-dimensional images. In contrast, most x-ray angiography systems can only acquire a series of two-dimensional projection images. MR has clear advantages when multiple projections or volume reformatting are required in order to understand the treatment of complex three-dimensional vascular abnormalities, such as arterial-venous malformations (AVMs) and aneurysms. Furthermore, MR is sensitive to measurement of a variety of "functional" parameters including temperature, blood flow, tissue perfusion, diffusion, and brain activation. This additional diagnostic information, which, in principle, can be obtained before, during and immediately after therapy, cannot be acquired by x-ray fluoroscopy alone. It is likely that once suitable MR-based endovascular procedures have been developed, the next challenge will be to integrate this functional information with conventional anatomical imaging and device tracking.

Currently, both "active" and "passive" approaches are being used for visualization and monitoring of the placement of devices and materials used for therapeutic procedures done using MR guidance. When active tracking is used, visualization is accomplished by incorporating one or more small radio-frequency (RF) coils into the device, e.g., a catheter.

The position of the device is computed from MR signals generated by these coils and detected by MR imager. This information is superimposed on an anatomical "road map" image of the area in which the device is being used. The advantages of active tracking include excellent temporal and spatial resolution. However, active methods allow visualization of only a discrete point(s) on the device. Typically, only the tip of the device is "active", i.e., visualized. Although it is possible to incorporate multiple RF coils (4–6 on typical clinical MR systems) into a device, it is still impossible to determine position at more than a few discrete points along the device. While this may be acceptable for tracking rigid biopsy needles, this is a significant limitation for tracking flexible devices such as those used in endovascular therapy. Furthermore, intravascular heating due to RF-induced currents is a concern with active methods.

The attachment of coils onto flexible catheters presents numerous challenges in maintaining the functionality of the catheter as these coils result in changes in the mechanical properties of the catheter onto which they are incorporated. Ladd et al. [Ladd et al., *Proc.* ISMRM (1997) 1937] have addressed some of the deficiencies of an active catheter by designing a RF coil that wraps about the catheter.

This allows visualization of a considerable length of a catheter, but still does not address the problems of RF heating and the mechanical changes which degrade catheter performance.

One technique for passive tracking is based on the fact that some devices do not emit a detectable MR signal and also cause no artifacts in the MR image. This results in such a device being seen as an area of signal loss or signal void in the MR images. By tracking or following the signal void, the position and motion of such a device can be determined. One advantage of passive tracking methods over active methods is that they do allow "visualization" of the entire length of a device. Since air, cortical bone and flowing blood are also seen in MR images as areas of signal voids, the use of signal void is generally not appropriate for tracking devices used in interventional MR. Another technique of passive tracking utilizes the fact that some materials cause a magnetic susceptibility artifact (either signal enhancement or signal loss) that causes a signal different from the tissue in which they are located. Some catheters braided with metal, some stents and some guide-wires are examples of such devices. One problem with the use of these techniques based on susceptibility artifacts is the fact that those used for localization of the device does not correspond precisely with the size of the device. This makes precise localization difficult.

A number of published reports describe passive catheter visualization schemes based on signal voids or susceptibility-induced artifacts. A principal drawback of these passive techniques is that visualization is dependent on the orientation of the device with respect to the main magnetic field.

Despite recognition and study of various aspects of the problems of visualization of medical devices in therapeutic, especially endovascular, procedures, the prior art has still not produced satisfactory and reliable techniques for visualization and tracking of the entire device in a procedure under MR guidance.

BRIEF SUMMARY OF THE INVENTION

The present invention provides a process for coating medical devices so that the devices are readily visualized, particularly, in $T_1$ weighted magnetic resonance images. Because of the high signal caused by the coating, the entirety of the coated devices can be readily visualized during, e.g., an endovascular procedure.

The foregoing, and other advantages of the present invention, are realized in a magnetic resonance (MR) signal-emitting coating which includes a paramagnetic metal ion-containing polymer complex and a method of visualizing medical devices in magnetic resonance imaging, which includes the step of coating the devices with the paramagnetic-ion containing polymer. Specifically, the present invention provides a coating for visualizing medical devices in magnetic resonance imaging, comprising a complex of formula (I):

wherein P is a polymer, X is a surface functional group, L is a chelate, M is a paramagnetic ion and n is an integer that is 2 or greater. The polymer P may be a base polymer from which a medical device is made.

In another aspect, the invention is a coating for visualizing medical devices in magnetic resonance imaging, comprising a complex of formula (II):

wherein P is a polymer, X is a surface functional group, L is a chelate, M is a paramagnetic ion, n is an integer that is 2 or greater and J is the linker or spacer molecule. The polymer P may be a base polymer from which a medical device is made.

In a further aspect, the invention is a magnetic resonance imaging system which includes a magnetic resonance device for generating a magnetic resonance image of a target object (as defined hereinafter) in an imaging region (as defined hereinafter) and an instrument for use with the target object in the imaging region. The instrument includes a body sized for use in the target object and a polymeric-paramagnetic ion complex coating in which the complex is represented by formula (I) through (V) as set forth below in the detailed description.

In yet another aspect, the invention is a method for visualizing medical devices in magnetic resonance imaging which includes the steps of (a) coating the medical device with a polymeric-paramagnetic complex of formula (I) through (V) as set forth below in the detailed description; (b) positioning the device within a target object; and (c) imaging the target object and coated device.

In a further aspect, the invention provides a method of making a medical device magnetic-resonance imageable. The method comprises providing a coating on the medical device in which a paramagnetic-metal ion/chelate complex is encapsulated by a first hydrogel. A chelate of the paramagnetic-metal-ion/chelate complex is linked to a functional group, and the functional group is an amino group or a carboxyl group. The paramagnetic-metal ion may, but need not be, designated as $M^{n+}$, wherein M is a lanthanide or a transition metal which is iron, manganese, chromium, cobalt or nickel, and n is an integer that is 2 or greater. In one embodiment, at least a portion of the medical device may be made from a solid-base polymer, and the method further comprises treating the solid-base polymer to yield the functional group thereon. Accordingly, the complex is covalently linked to the medical device. In another embodiment, the functional group may be a functional group of a polymer that is not covalently linked to the medical device. In a different embodiment, the functional group may be a functional group of a second hydrogel. The first and second hydrogels may be the same or different. A cross-linker may also be used to cross-link the first hydrogel with the solid-base polymer, the polymer not covalently linked to the medical device or the second hydrogel, depending upon the embodiment.

In another aspect, the invention provides a medical device capable of being magnetic-resonance imaged. The device comprises a chelate linked to a functional group. The functional group may be an amino or a carboxyl group. The device also comprises a paramagnetic-metal ion that is coordinated with the chelate to form a paramagnetic-metal-ion/chelate complex. The device also comprises a first hydrogel that encapsulates the paramagnetic-metal-ion/chelate complex. The paramagnetic-metal ion may, but need not be, designated as $M^{n+}$, wherein M is a lanthanide or a transition metal which is iron, manganese, chromium, cobalt or nickel, and n is an integer that is 2 or greater. In one embodiment, at least a portion of the medical device may be made from a solid-base polymer, and the functional group is a functional group on the solid-base polymer. Accordingly, the complex is covalently linked to the medical device. In another embodiment, the functional group may be a functional group of a polymer that is not covalently linked to the medical device. In a different embodiment, the functional group may be a functional group of a second hydrogel. The first and second hydrogels may be the same or different. A cross-linker may also be used to cross-link the first hydrogel with the solid-base polymer, the polymer not covalently linked to the medical device or the second hydrogel, depending upon the embodiment.

In yet another aspect, the invention provides a method of reducing the mobility of paramagnetic metal ion/chelate complexes covalently linked to a solid polymer substrate of a medical device. This method includes providing a medical device having paramagnetic metal ion/chelate complexes covalently linked to the solid polymer substrate of the medical device. The method also includes encapsulating at least a portion of the medical device having at least one of the paramagnetic metal ion/chelate complexes covalently linked thereto with a hydrogel. The hydrogel reduces the mobility of at least one of the paramagnetic metal ion/chelate complexes, and thereby enhances the magnetic resonance imageability of the medical device.

In a further aspect, the invention provides a method of manufacturing a magnetic-resonance-imageable medical device. The method comprises providing a medical device and cross-linking a chain with a first hydrogel to form a hydrogel overcoat on at least a portion of the medical device. The paramagnetic-metal-ion/chelate complex is linked to the chain. The paramagnetic-metal ion may, but need not be, designated as $M^{n+}$, wherein M is a lanthanide or a transition metal which is iron, manganese, chromium, cobalt or nickel, and n is an integer that is 2 or greater. The chain may be a polymer chain or a hydrogel. In one embodiment, the medical device has a surface, and the surface may be at least partially made from or coated with a solid-base polymer, which includes the polymer chain. The complex is thereby covalently linked to the medical device. In another embodiment, the polymer chain is not linked to the medical device. In yet another embodiment, the chain is a second hydrogel.

Other advantages and a fuller appreciation of the specific attributes of this invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF THE DRAWINGS

The preferred exemplary embodiment of the present invention will hereinafter be described in conjunction with the appended drawing wherein like designations refer to like elements throughout and in which:

FIG. 8 shows the chemical synthesis of linking DTPA[Gd(III)] to the surface of a polymer-based medical device and the encapsulation of the device with a hydrogel.

FIG. 13 shows the chemical structure of a MR signal-emitting coating polymer-based medical device in which DTPA[Gd(III)] was attached on the device surface, and then encapsulated by a cross-linked hydrogel.

FIG. 14 shows the chemical details for the example schematically represented in FIG. 13.

FIG. 15 is a MR maximum-intensity-projection (MIP) image, using a 3D RF spoiled gradiant-recalled echo (SPRG) sequence in a live canine aorta, of an example of the second embodiment of the invention shown in FIG. 13 with dry thickness of the entire coating of 60 μm. The length of coated PE rod is about 40 cm with a diameter of about 2 mm. The image was acquired 25 minutes after the rod was inserted into the canine aorta.

FIG. 16 shows the chemical structure of a MR signal-emitting hydrogel coating on the surface of a medical device in which a DTPA[Gd(III)] linked primary polymer was dispersed and cross-linked with hydrogel.

FIG. 17 shows the chemical details for the example schematically represented in FIG. 16.

FIG. 18 is a MR maximum-intensity-projection (MIP) image, using a 3D RF spoiled gradiant-recalled echo (SPRG) sequence in a live canine aorta, of an example of the third embodiment of the invention shown in FIG. 16 with dry thickness of the entire coating of about 60 μm, but with a guide-wire instead of polyethylene. The length of coated guide wire is about 60 cm with the diameter of about 0.038 in. The image was acquired 10 minutes after the guide-wire was inserted into the canine aorta.

FIG. 19 shows the chemical structure of a MR signal-emitting hydrogel coating on the surface of a medical device in which a DTPA[Gd(III)] linked hydrogel, gelatin, was dispersed and cross-linked.

FIG. 20 shows the chemical details for the example schematically represented in FIG. 19.

FIG. 21 shows a MR maximum-intensity-projection (MIP) image, using a 3D RF spoiled gradiant-recalled echo (SPRG) sequence in a live canine aorta, of the example of the fourth embodiment of the invention shown in FIG. 19 with dry thickness of the entire coating of 60 μm, but with a guide-wire instead of polyethylene. The length of coated guide wire is about 60 cm with the diameter of about 0.038 in. The image was acquired 30 minutes after the rod was inserted into the canine aorta.

FIG. 22 shows a MR maximum-intensity-projection (MIP) image, using a 3D RF spoiled gradiant-recalled echo (SPRG) sequence in a live canine aorta, of the example of the fourth embodiment of the invention shown in FIG. 19 with dry thickness of the entire coating of 30 μm, but with a guide wire instead of polyethylene. The length of coated guide wire is about 45 cm with a diameter of about 4 F. The image was acquired 20 minutes after the rod was inserted into the canine aorta.

DETAILED DESCRIPTION OF THE INVENTION

Figure 1:
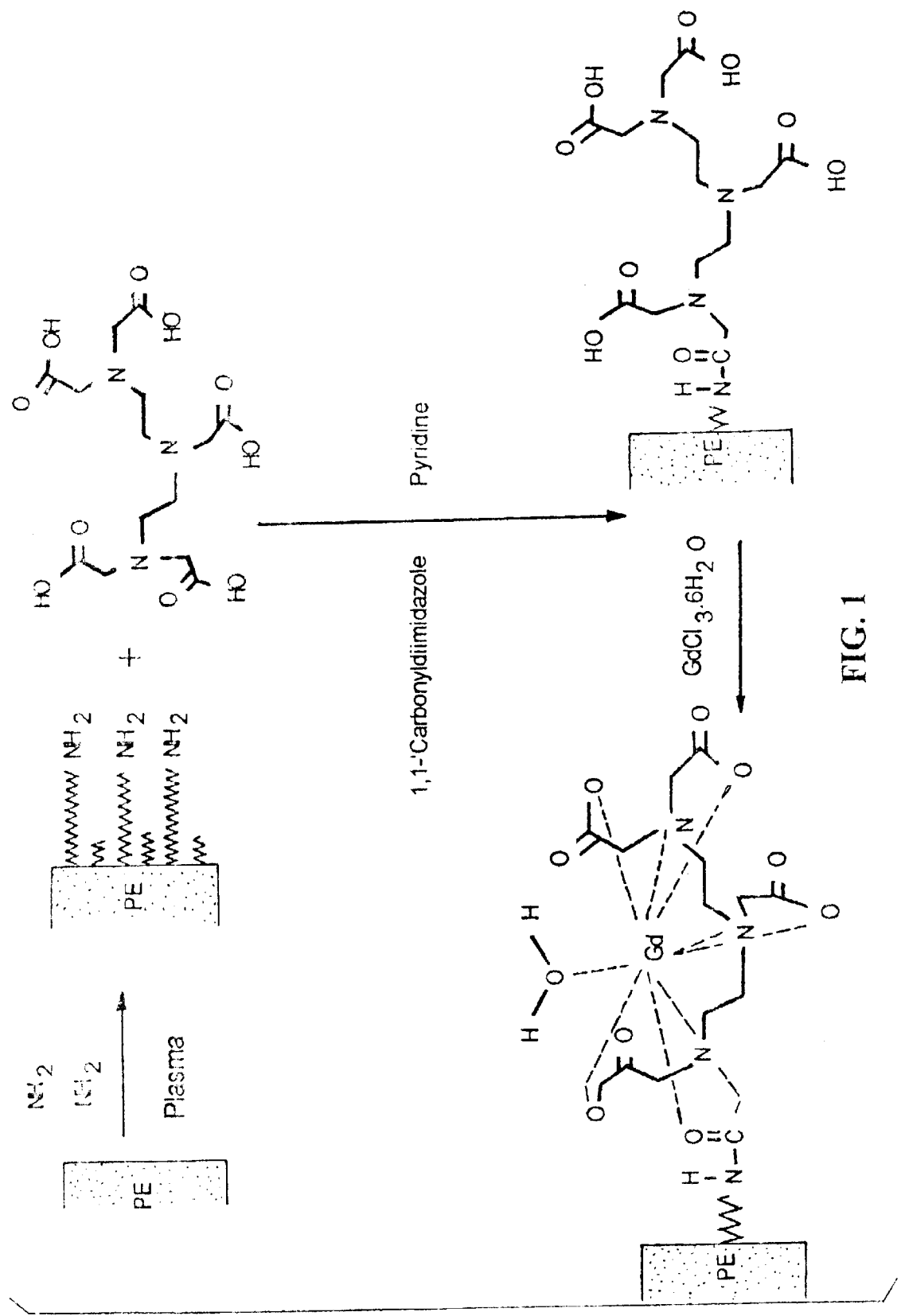
FIG. 1 is a schematic representation of the three-step coating method in accordance with the present invention.

The present invention relates broadly to coating that are capable of emitting magnetic resonance signals. The present invention is most particularly adapted for use in coating medical devices so that they are readily visualized in magnetic resonance images. Accordingly, the present invention will now be described in detail with respect to such endeavors; however, those skilled in the art will appreciate that such a description of the invention is meant to be exemplary only and should not be viewed as restrictive of the full scope thereof.

The present invention provides coatings containing paramagnetic ions. The coatings of the present invention are characterized by an ability to emit magnetic resonance signals and to permit visualization of the entirety of a device or instrument so coated as used in interventional MR procedures. The coatings are also of value for providing improved visibility in interoperative MR of surgical instruments after being coated with the signal-enhancing coatings of the present invention. The improved visualization of implanted devices so coated, e.g., stents, coils and valves, may find a whole host of applications in diagnostic MR. These attributes of the coating in accordance with the present invention are achieved through a novel combination of physical properties and chemical functionalities.

In the following description of the method of the invention, coating-process steps are carried out at room temperature (RT) and atmospheric pressure unless otherwise specified.

Throughout the specification, the term "medical device" is used in a broad sense to refer to any tool, instrument or other object (e.g., a catheter, biopsy needle, stent etc.) employed to perform or be useful in performing an operation on a target, or a device which itself is implanted in the body (human or animal) for some therapeutic purpose, e.g., a stent, a graft, etc., and a "target" or "target object" being all or part of a human patient or animal positioned in the "imaging region" of a magnetic resonance imaging system (the "imaging region" being the space within an MRI system in which a target can be imaged). "Medical device" may also refer to a guide-wire.

Of particular interest are endovascular procedures performed under MR guidance. Such endovascular procedures include the treatment of partial vascular occlusions with balloons, arterial-venous malformations with embolic agents, aneurysms with stents or coils, as well as sub-arachnoid hemorrhage (SAH)-induced vasospasm with local applications of papaverine. In these therapeutic procedures, the device or agent is delivered via the lumen of a catheter, the placement of which has traditionally relied on, to varying degrees, x-ray fluoroscopic guidance.

In one aspect, the present invention provides a method of coating the surface of medical devices with a coating which is a polymeric material containing a paramagnetic ion, which coating is generally represented by formula (I):

$$P\text{---}X\text{---}L\text{---}M^{n+} \qquad (I)$$

wherein P is a polymer, X is a surface functional group such as an amino or a carboxyl group, L is a chelate, M is a paramagnetic ion which binds to L, and n is an integer that is 2 or greater. P, more specifically, may be a base polymer substrate from which the medical device is made. It is understood that a medical device may be suitably constructed of a polymer whose surface is then functionalized with X, or a medical device may be suitably coated with a polymer whose surface is then appropriately functionalized. Such methods for coating are generally known in the art.

To enhance the rotational mobility of $M^{n+}$ the coating optionally contains a linker or spacer molecule J, and is generally represented by the formula (II):

$$P\text{---}X\text{---}J\text{---}L\text{---}M^{n+} \qquad (II)$$

wherein P, X, L and M are as described above and J is the linker or spacer molecule which joins the surface functional group X and the chelate L, i.e., J is an intermediary between the surface functional group and the chelate.

P is suitably any polymer including, but not limited to, polyethylene, polypropylene, polyesters, polycarbonates, polyamides such as Nylon™, polytetrafluoroethylene (Teflon™) and polyurethanes that can be surface functionalized with an X group. Other polymers include, but are not limited to, polyamide resins (more particularly, 0.5 percent), polyamino undecanoic acid, polydimethylsiloxane (viscosity 0.65 centistokes), polyethylene glycol (200, 600, 20,000), polyethylene glycol monoether, polyglycol nitroterephthalate, polyoxyethylene lauryl ether, polyoxyl 10 castor oil, polypropylene glycol, polysorbate 60, a mixture of stearate and palmitate esters of sorbitol copolymerized with ethylene glycol, polytetrafluoroethylene, polyvinyl acetate phthalate, polyvinyl alcohol and polystyrene sulfonate. It is noted that some polymer surfaces may need to be coated further with hydrophilic layers. P in the above formula represents a base solid polymer which may stand for an extant medical device such as a catheter.

J is suitably a bifunctional molecule, e.g., a lactam having an available amino group and a carboxyl group, an α,ω-diamine having two available amino groups or a fatty acid anhydride having two available carboxyl groups. J may also be a cyclic amide or α, ω-diamine having two available amino groups. J covalently connects chelate L to surface functional group X.

X is suitably an amino or carboxyl group.

L is suitably any chelate which has a relatively high (e.g., $>10^{20}$) stability constant, K, for the chelate-paramagnetic ion complex. Such chelates include but are not limited to diethylenetriaminepentaacetic acid (DTPA), 1,4,7,10-tetracyclododecane-N,N',N'',N'''-tetraacetic acid (DOTA) and 1,4,8,11-tetraazacyclotradecane-N,N',N'',N'''-tetraacetic acid (TETA). Other chelates may include diethylenetriaminepentaacetic acid-N,N'-bis(methylamide) (DTPA-BMA), diethylenetriaminepentaacetic acid-N,N'-bis(methoxyethylamide) (DTPA-BMEA), s-4-(4-ethoxybenzyl)-3,6,9-tris[(carboxylatomethyl)]-3,6,9-triazaundecanedionic acid (EOB-DTPA), benzyloxypropionictetraacetate (BOPTA), (4R)-4-[bis(carboxymethylamino)]-3,6,9-triazaundecanedionic acid (MS-325), 1,4,7-tris(carboxymethyl)-10-(2'-hydroxypropyl)-1,4,7,10-tetraazacyclododecane (HP-DO3A), and DO3A-butrol.

The structures of some of these chelates follow:

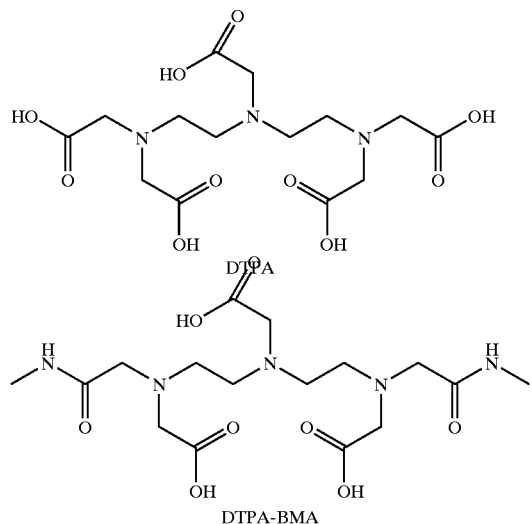

DTPA

DTPA-BMA

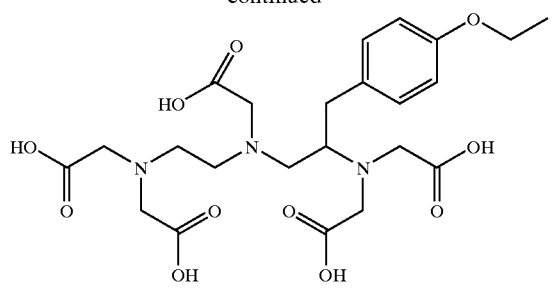

EOB-DTPA

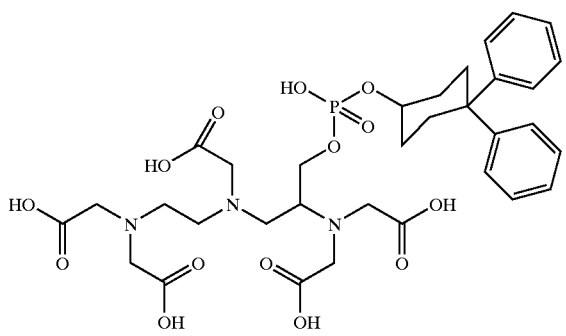

MS-325-L

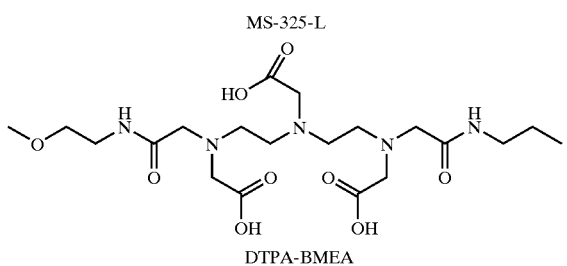

DTPA-BMEA

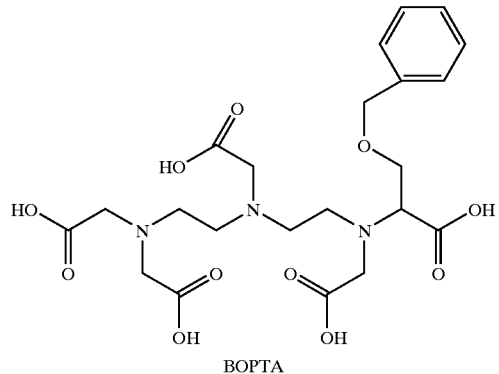

BOPTA

As used herein, the term "paramagnetic-metal-ion/chelate complex" is meant to refer to a complex comprising one or more paramagnetic-metal ions ($M^{n+}$) coordinated with or bound to a chelate L. The paramagnetic-metal-ion/chelate complex may comprise any of the paramagnetic-metal ions or chelates discussed above and below. The paramagnetic-metal-ion/chelate complex may be designated by the following in the formulas described above and below: $L-M^{n+}$.

As used herein, the term "chain" is meant to refer to a group of one or more atoms. The chain may be a group of atoms that are part of a polymer or part of a hydrogel. The chain may also be a solid-base polymer, a polymer that is not covalently linked to a medical device or a second hydrogel.

The paramagnetic metal ion is suitably a multivalent ion of paramagnetic metal including but not limited to the lanthanides and transition metals such as iron, manganese, chromium, cobalt and nickel. Preferably, $M^{n+}$ is a lanthanide which is highly paramagnetic, most preferred of which is the gadolinium(III) ion having seven unpaired electrons in the 4f orbital. It is noted that the gadolinium(III) (Gd (III)) ion is often used in MR contrast agents, i.e., signal influencing or enhancing agents, because it is highly paramagnetic and has a large magnetic moment due to the seven unpaired 4f orbital electrons. In such contrast agents, gadolinium(III) ion is generally combined with a chelating agent, such as DTPA. The resulting complex (Gd-DTPA or Magnevist; Berlex Imaging, Wayne, N.J.) is very stable in vivo, and has a stability constant of $10^{23}$, making it safe for human use. Similar agents have been developed by chelating the gadolinium(III) ion with other complexes, e.g., MS-325, Epix Medical, Cambridge, Mass. The gadolinium (III) causes a localized $T_1$ reduction in the water protons in its environment, giving enhanced visibility in $T_1$ weighed MR images. Because of the high signal caused by the coating by virtue of shortening of $T_1$, the entirety of the coated devices can be readily visualized during, e.g., an endovascular procedure.

The MR signal-emitting coatings in accordance with the present invention are synthesized according to a three or four-step process. The three-step method includes: (i) plasma-treating the surface of a polymeric material (or a material coated with a polymer) to yield surface functional groups, e.g., using a nitrogen-containing gas or vapor such as hydrazine ($NH_2NH_2$) to yield amino groups; (ii) binding a chelating agent, e.g., DTPA, to the surface functional group (e.g. through amide linkage); and (iii) coordinating a functional paramagnetic metal ion such as Gd(III) with the chelating agent. Alternatively, the surface may be coated with amino-group-containing polymers which can then be linked to a chelating agent. Generally, the polymeric material is a solid-base polymer from which the medical device is fabricated. It is noted that the linkage between the surface functional groups and the chelates is often an amide linkage. In addition to hydrazine, other plasma gases which can be used to provide surface functional amino groups include urea, ammonia, a nitrogen-hydrogen combination or combinations of these gases. Plasma gases which provide surface functional carboxyl groups include carbon dioxide or oxygen.

The paramagnetic-metal-ion/chelate complex is covalently bonded to the medical device such that the complex is substantially non-absorbable by a living organism upon being inserted therein. The complex is also substantially non-invasive within the endovascular system or tissues such that non-specific binding of proteins are minimized. The complex of the present invention differs substantially from other methods in which a liquid contrasting agent is merely applied to a medical device. In other words, such a liquid contrasting agent is not covalently linked to the device, and therefore, is likely to be absorbed by the tissue into which it is inserted.

A schematic reaction process of a preferred embodiment of the present invention is shown in FIG. 1. As seen specifically in FIG. 1, polyethylene is treated with a hydrazine plasma to yield surface functionalized amino groups. The amino groups are reacted with DTPA in the presence of a coupling catalyst, e.g.,1,1'-cabonyldiimidazole, to effect an amide linkage between amino groups and DTPA. The surface amino-DTPA groups are then treated with gadolinium trichloride hexahydrate in an aqueous medium, coordinating the gadolinium (III) ion with the DTPA.

The MR-signal-emitting coatings are suitably made via a four-step process which is similar to the three-step process except that prior to step (ii), i.e., prior to reaction with the chelating agent, a linker agent or spacer molecule, e.g., a lactam, is bound to the surface functional groups, resulting in the coating is of formula (II).

Figure 2:
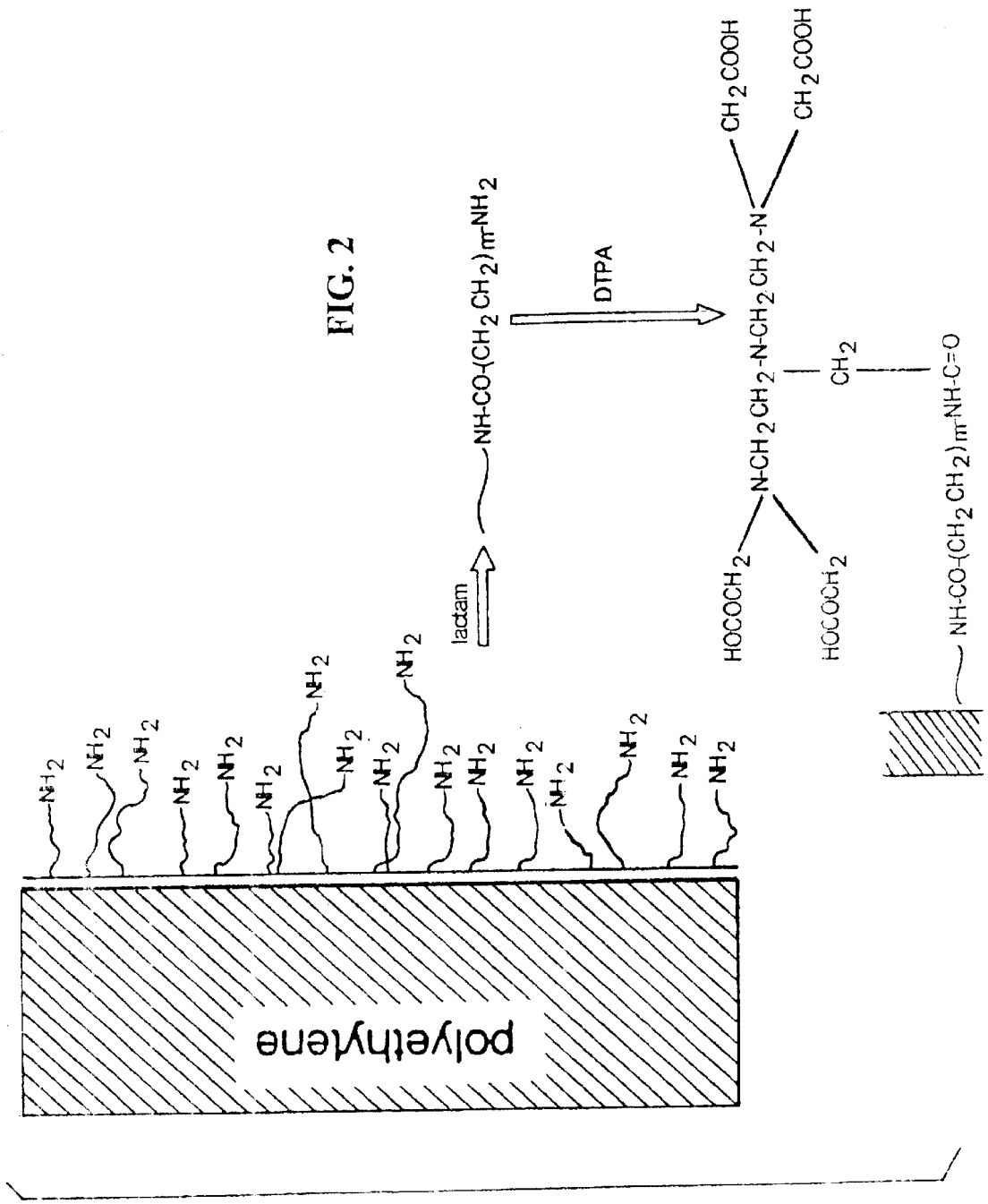
FIG. 2 is a schematic representation of the four-step coating method using a linker agent.

An illustrative schematic reaction process using a lactam or cyclic amide is shown in FIG. 2. As seen in FIG. 2, a polyethylene with an amino functionalized surface is reacted with a lactam. The amino groups and lactam molecules are coupled via an amide linkage. It is noted that "m" in the designation of the amino-lactam linkage is suitably an integer greater than 1. The polyethylene-amino-lactam complex is then reacted with DTPA which forms a second amide linkage at the distal end of the lactam molecule. The last step in the process, coordinating the gadolinium (III) ion with the DTPA (not shown in FIG. 2), is the same as shown in FIG. 1.

Figure 3A:
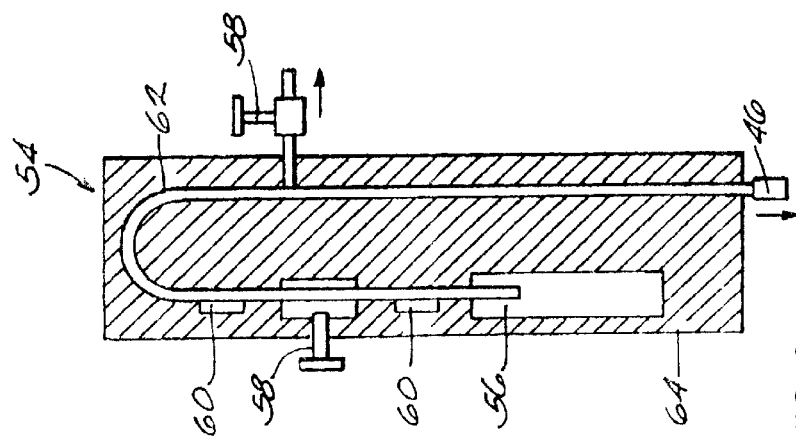
FIGS. 3 and 3A are schematic representations of a capacitively coupled RF plasma reactor for use in the method of the present invention, FIG. 3A being an enlarged view of the vapor supply assemblage of the plasma reactor of FIG. 3.
Figure 3:
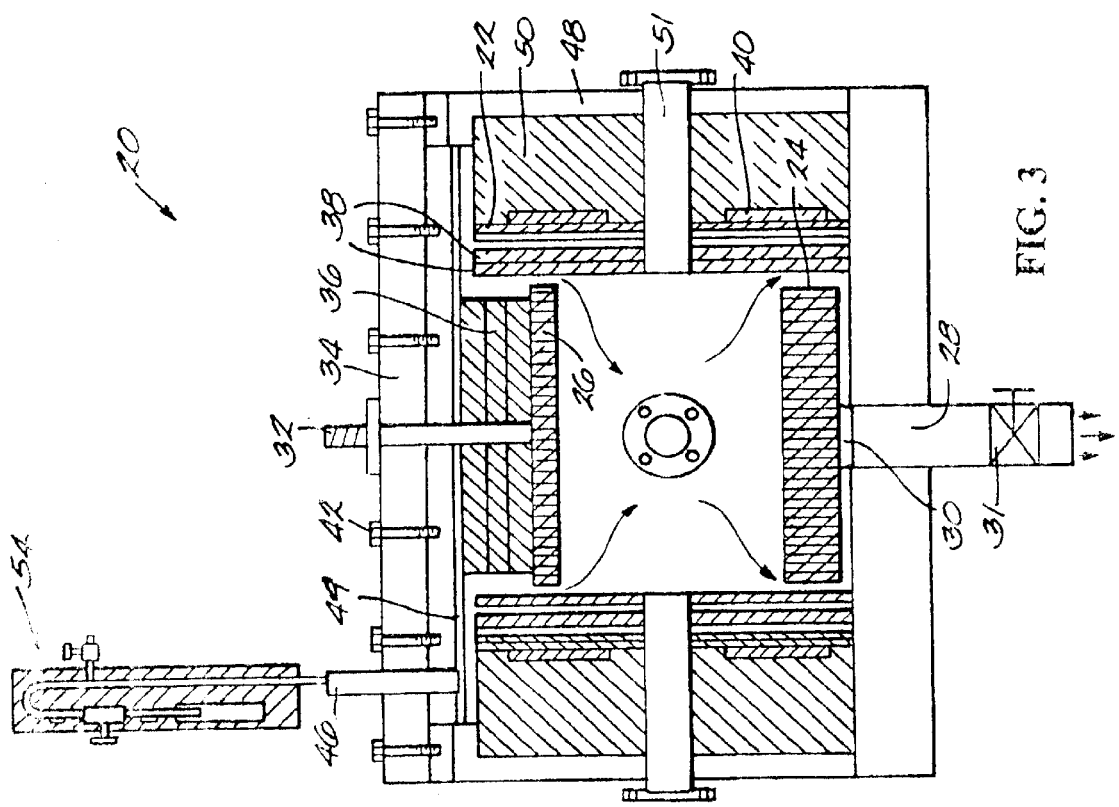

Specific reaction conditions for forming a coating in accordance with the present invention, which utilizes surface functionalized amino groups, include plasma treatment of a polymeric surface, e.g., a polyethylene surface, at 50 W power input in a hydrazine atmosphere within a plasma chamber, schematically represented in FIG. 3, for 5–6 min. under 13 Pa to 106 Pa (100 mT–800 mT).

As seen in FIG. 3, an exemplary plasma chamber, designated generally by reference numeral 20, includes a cylindrical stainless steel reaction chamber 22 suitably having a 20 cm diameter, a lower electrode 24, which is grounded, and an upper electrode 26, both suitably constructed of stainless steel. Electrodes 24 and 26 are suitably 0.8 cm thick. Upper electrode 26 is connected to an RF-power supply (not shown). Both electrodes are removable which facilitates post-plasma cleaning operations. Lower electrode 24 also forms part of a vacuum line 28 through a supporting conical-shaped and circularly-perforated stainless steel tubing 30 that has a control valve 31. The evacuation of chamber 22 is performed uniformly through a narrow gap (3 mm) existing between lower electrode 24 and the bottom of chamber 22. Upper electrode 26 is directly connected to a threaded end of a vacuum-tight metal/ceramic feedthrough 32 which assures both the insulation of the RF-power line from the reactor and the dissipation of the RF-power to the electrodes. A space 34 between upper electrode 26 and the upper wall of chamber 22 is occupied by three removable 1 cm thick, 20 cm diameter Pyrex™ glass disks 36. Disks 36 insulate upper electrode 26 from the stainless steel top of the reactor 20 and allow the adjustment of the electrode gap. The reactor volume located outside the perimeter of the electrodes is occupied by two Pyrex™ glass cylinders 38 provided with four symmetrically located through-holes 40 for diagnostic purposes.

This reactor configuration substantially eliminates the non-plasma zones of the gas environment and considerably reduces the radial diffusion of the plasma species, consequently leading to more uniform plasma exposure of the substrates (electrodes). As a result, uniform surface treatment and deposition processes (6–10% film thickness variation) can be achieved.

The removable top part of the reactor 20 vacuum seals chamber 22 with the aid of a copper gasket and fastening bolts 42. This part of the reactor also accommodates a narrow circular gas-mixing chamber 44 provided with a shower-type 0.5 mm diameter orifice system, and a gas- and monomer supply connection 46. This gas supply configuration assures a uniform penetration and flow of gases and vapors through the reaction zone. The entire reactor 20 is thermostated by electric heaters attached to the outside surface of chamber 22 and embedded in an aluminum sheet 48 protecting a glass-wool blanket 50 to avoid extensive loss of thermal energy.

For diagnostic purposes, four symmetrically positioned stainless steel port hole tubings 51 are connected and welded through insulating blanket 50 to the reactor wall. These port holes are provided with exchangeable, optically smooth, quartz windows 52. A vapor supply assemblage 54, as seen in FIG. 3A, includes a plasma reservoir 56, valves 58, VCR connectors 60 and connecting stainless steel tubing 62. Assemblage 54 is embedded in two 1 cm thick copper jackets 64 20 provided with controlled electric heaters to process low volatility chemicals. Assemblage 54 is insulated using a glass-wool blanket coating. The thermostatic capabilities of reactor 20 are in the range of 25–250° C.

Once the device to be coated is surface functionalized, it is then immersed in a solution of the chelating agent, e.g., DTPA, in, e.g., anhydrous pyridine, typically with a coupling catalyst, e.g., 1,1'-carbonyldiimidazole, for a time sufficient for the chelate to react with the amine groups, e.g., 20 hours. The surface is washed sequentially with at least one of the following solvents: pyridine, chloroform, methanol and water. The chelate-treated surface is then soaked in an aqueous solution of $GdCl_3 6H_2O$, for a time sufficient for the paramagnetic ion to react with the chelate, e.g., 12 hours. The surface is then washed with water to remove any uncoordinated, physisorbed Gd(III) ion.

In test processes, each step has been verified to confirm that the bonding, in fact, occurs. For example, to verify the amino group functionalization, x-ray photoelectron spectroscopy (XPS) was used. A XPS spectrum of the polyethylene surface was taken prior to and after plasma treatment. The XPS spectrum of polyethylene before the treatment showed no nitrogen peak. After treatment, the nitrogen peak was 5.2% relative to carbon and oxygen peaks of 63.2% and 31.6%, respectively.

To determine whether the amino groups were accessible for chemical reactions, after step (i) the surface was reacted with p-trifluorobenzaldehyde or p-fluorophenone propionic acid and rinsed with a solvent (tetrahydrofuran). This reactant, chosen because of good sensitivity of fluorine atoms to XPS, produces many photoelectrons upon x-ray excitation. The result of the XPS experiment showed a significant fluorine signal. The peaks for fluorine, nitrogen, carbon and oxygen were: 3.2%, 1.5%, 75.7% and 19.6%, respectively. This demonstrated that the amino groups were accessible and capable of chemical reaction.

Because the coatings in accordance with the present invention are advantageously applied to catheters and because a catheter surface is cylindrical, it is noted that to coat commercial catheters, the plasma reaction must be carried out by rotating the catheter axis normal to the plasma sheath propagation direction. Such rotational devices are known and can be readily used in the plasma reactor depicted in FIG. 3. To verify that surface amination occurs for such surfaces, atomic force microscopy (AFM) is used to study the surface morphology because XPS requires a well-defined planar surface relative to the incident X-ray. The coating densities (e.g., nmol $Gd^{3+}/m^2$) are measured using NMR and optimal coating densities can be determined.

It is also understood that metallic surfaces can be treated with the coatings in accordance with the present invention. Metallic surfaces, e.g., guide-wires, can be coated with the polymers set forth above, e.g., polyethylene, by various known surface-coating techniques, e.g., melt coating, a well known procedure to overcoat polymers on metal surfaces. Once the metallic surfaces are overcoated with polymer, all other chemical steps as described herein apply. In an example to be described below, we used commercial guide-wires which were previously coated with hydrophilic polymers.

In a second embodiment of the invention, the magnetic resonance imageability of medical devices is enhanced or improved by encapsulating the medical device, or paramagnetic-metal-ion/chelate complexes linked thereto, with a hydrogel. As discussed above, catheters and other medical devices may be at least partially made or coated with a variety of polymers. The polymer surfaces of the existing medical devices are functionalized by plasma treatment or by melt coating with a hydrophilic polymer as discussed above or precoating with a hydrophilic polymer containing primary amine groups. Through amide linkage or α,ω-diamide linkage via a linker molecule, a chelating agent may be covalently bonded to the functionalized polymer surface. Subsequently, any of the paramagnetic-metal ions discussed above, e.g. Gd(III), can be complexed to the chelate. The necessary contrast for MRI is the result of interactions of protons in body fluid (e.g., blood) or bound within the encapsulating hydrogel with the highly magnetic ion, and the resulting shortening of $T_1$ relaxation time of the proton. It has been discovered that by reducing the mobility of the paramagnetic-metal-ion/chelate complex without affecting the exchange rate of one molecule of water coordinating to the paramagnetic metal ion, the MR-imageability of the medical device is enhanced and improved. In other words, if the movement of these complexes is restricted, the MR-imageability of the polymer to which the complex is attached is greatly improved.

Therefore, it has been found that one way by which to reduce the mobility of the complex for imaging is to encapsulate the medical device, and more particularly, the complex in a hydrogel. The hydrogel reduces the mobility of the paramagnetic-metal-ion/chelate complexes without significantly affecting the rate of water molecule exchange on the complexes, thereby enhancing the magnetic-resonance imageability of the medical devices. There is a delicate balance between slowing of the rotational relaxation time of the paramagnetic-metal-ion/chelate complexes and retardation of the exchange rate of water molecules from inner coordination sphere of the $M^{n+}$ to the bulk water molecules diffusing in the outer coordination sphere of $M^{n+}$. The reason for MR imageability for free paramagnetic-metal-ion/chelate complexes without being bonded to polymer surface comes about because of a much greater concentration of the complex in solution compared with that bound to the surface.

Examples of suitable hydrogels include, but are not limited to, at least one of collagen, gelatin, hyaluronate, fibrin, alginate, agarose, chitosan, poly(acrylic acid), poly(acrylamide), poly(2-hydroxyethyl methacrylate), poly(N-isopropylacrylamide), poly(ethylene glycol)/poly(ethylene oxide), poly(ethylene oxide)-block-poly(lactic acid), poly(vinyl alcohol), polyphosphazenes, polypeptides and combinations thereof. Any hydrogel or similar substance which reduces the mobility of the paramagnetic-metal-ion/chelate complex can also be used, such as physical hydrogels that can be chill-set without chemical cross-linking. In addition, overcoating of high molecular weight, hydrophilic polymers can be used, e.g., poly(acrylic acid), poly(vinyl alcohol), polyacrylamide, having a small fraction of functional groups that can be linked to residual amino groups are suitable for use with the invention. The MR-imageability of other MR-imageable devices made by methods other than those described herein may also be improved by coating other devices with the hydrogels described above.

The devices can be encapsulated using a variety of known encapsulating techniques in the art. For example, a gel may be melted into a solution, and then the device dipped into the solution and then removed. More particularly, the gel may be dissolved in distilled water and heated. Subsequently, the solution coating the device is allowed to dry and physically self assemble to small crystallites that may adsorb to the polymer surface of the medical device and also play the role of cross-links. Such a phenomenon is commonly referred to as "chill-set" since it arises from thermal behavior of gelling systems.

The gel may also be painted onto the medical device. Alternatively, the medical device may be encapsulated by polymerization of a hydrophilic monomer with a small fraction of cross-linker that participates in the polymerization process. For example, a medical device may be immersed in a solution of acrylamide monomer with bisacrylamide as the cross-linker and a photo-initiator, and the polymerization is effected with ultra-violet (UV) irradiation to initiate the polymerization in a cylindrical optical cell.

Alternatively, the medical device may be dipped into a gelatin solution in a suitable concentration (e.g., 5%), and mixed with a cross-linker such as glutaraldehyde. As used herein, the term "cross-linker" is meant to refer to any multi-functional chemical moiety which can connect two or a greater number of polymer chains to produce a polymeric network. Other suitable cross-linkers include, but are in no way limited to, BVSM (bis-vinylsulfonemethane) and BVSME (bis-vinylsulfonemethane ether). Any substance that is capable of cross-linking with the hydrogels listed above is also suitable for use with the invention. Upon removing the device from the gelatin solution and letting it dry, the cross-linking takes place to encapsulate the entire coated assembly firmly with a sufficient modulus to be mechanically stable.

Typically, encapsulation is repeated until the desired thickness of the gel is obtained. The thickness of the encapsulated-hydrogel layer may be about 10 to about 60 microns, although it may be less and it may be more. In other words, the surface may be "primed" and then subsequently "painted" with a series of "coats" of gel until the desired thickness of the gel layer is obtained. Alternatively, the gel concentration is adjusted to bring about the desired thickness in a single coating process. In order to test the effectiveness of coating these devices with hydrogels to enhance the MR-imageability of the medical device, three samples were prepared and tested as set forth and fully described in Example 10 below.

Figure 13:
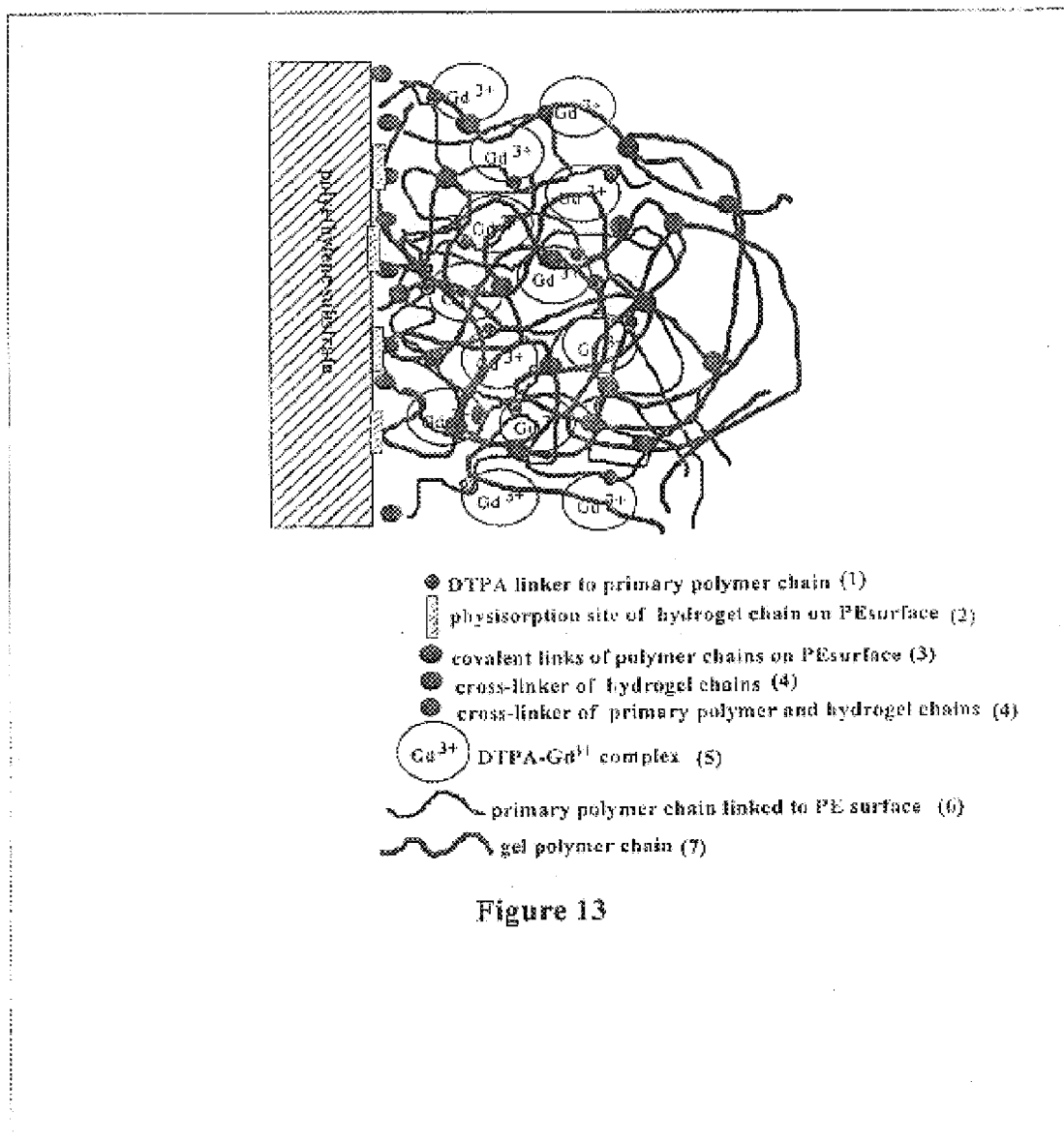
FIG. 13 is a schematic representation of one example of the second embodiment of the invention, wherein a polyethylene rod surface coated with amine-linked polymers is chemically linked with DTPA, which is coordinated with Gd(III). The rod, polymer, DTPA and Gd(III) are encapsulated with a soluble gelatin, which is cross-linked with glutaraldehyde to form a hydrogel overcoat. In other words.

Example 11 below also describes in more detail how one example of the second embodiment of the invention can be made. Moreover, FIG. 13 is a schematic representation of one example of the second embodiment of the invention, wherein a polyethylene rod, surface coated with amine-linked polymers, is chemically linked with DTPA, which is coordinated with Gd(III). The rod, polymer, DTPA and Gd(III) are encapsulated with a soluble gelatin, which is cross-linked with glutaraldehyde to form a hydrogel overcoat. FIG. 14 shows the chemical details for the example schematically represented in FIG. 13.

The second embodiment may be summarized as a coating for improving the magnetic-resonance imageability of a medical device comprising a complex of formula (III). The method includes encapsulating at least a portion of the device having at least one of the paramagnetic-metal-ion/chelate complexes covalently linked thereto with a hydrogel. The complex of formula (III) follows:

$$(P-X-L-M^{n+})_{gel} \qquad (III),$$

wherein P is a base polymer substrate from which the device is made or with which the device is coated; X is a surface functional group; L is a chelate; M is a paramagnetic ion; n is an integer that is 2 or greater; and subscript "gel" stands for a hydrogel encapsulate.

In a third embodiment of the invention, a polymer having functional groups is chemically linked with one or more of the chelates described above. More particularly, the polymer having a functional group (e.g. an amino or a carboxyl group) is chemically linked to the chelate via the functional group. In addition to the polymers set forth above, an example of a suitable polymer having functional groups is, but should not be limited to, poly(N[3-aminopropyl] methacrylamide), which has the following repeating unit structure:

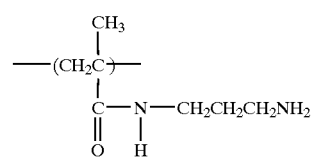

The third embodiment alleviates the need for a precoated polymer material on the medical device, or a medical device made from a polymer material. In other words, the third embodiment alleviates the need to link the paramagnetic-metal-ion/chelate complex to the surface of the medical device, when the medical device is made from or coated with a polymer. Instead, the polymer having functional groups, preferably poly(N[3-aminopropyl] methacrylamide), can be synthesized separately and then covalently linked to the chelate (e.g. DTPA) through functional groups (e.g. amine groups) on the polymer. Instead of linking the complex to the surface of the medical device, the polymer and complex are coordinated separately, and then added to a hydrogel. The chelate may be coordinated with the paramagnetic-metal ion (e.g. Gd(III)), and then mixed with soluble gelatin and used to coat a bare (i.e. uncoated) polyethylene rod. Subsequently, the gelatin is chill-set and then the binary matrix of gelatin and polymer may be cross-linked with a cross-linker such as glutaraldehyde. The polymer used in connection with this embodiment may be a poly(N[3-aminopropyl] methacrylamide), the chelate may be DTPA and the paramagnetic-metal ion may be Gd(III). In addition, the hydrogel may be gelatin and the cross-linker may be glutaraldehyde. Typically, the surface of the medical device may be polyethylene. Again, in addition to these specific compounds, any of the polymers, chelates, paramagnetic-metal ions, hydrogels and cross-linkers discussed above are also suitable for use with this embodiment of the invention.

Figure 16:
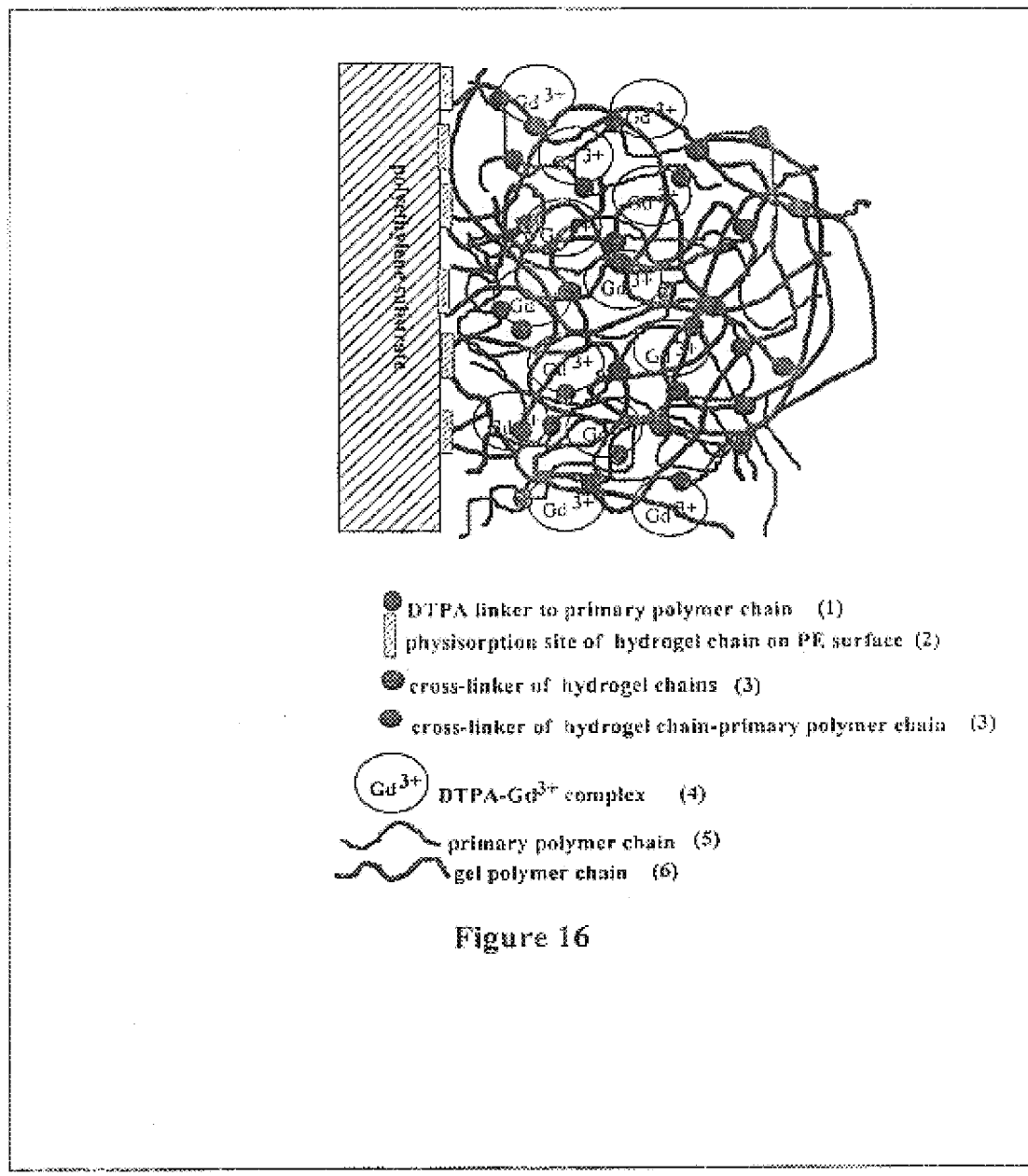
FIG. 16 is a schematic representation of one example of the third embodiment of the invention, wherein a polymer with an amine functional group is chemically linked with DTPA, coordinated with Gd(III) and mixed with soluble gelatin. The resulting mixture is applied onto a medical device surface without prior treatment and cross-linked with glutaraldehyde to form a hydrogel overcoat. In other words.

Example 12 below describes in more detail how one example of the third embodiment of the invention can be made. FIG. 16 is a schematic representation of one example of the third embodiment of the invention, wherein a polymer is chemically linked with DTPA, coordinated with Gd(III) and mixed with soluble gelatin. The resulting mixture is applied to a bare (i.e. uncoated) polyethylene surface and cross-linked with glutaraldehyde to form a hydrogel overcoat. FIG. 17 shows the chemical details for the example schematically represented in FIG. 16.

The third embodiment may be summarized as a coating for visualizing medical devices in magnetic resonance imaging comprising a complex of formula (IV). The method includes encapsulating at least a portion of the medical device with a hydrogel, wherein at least one of the paramagnetic-metal-ion/chelate complexes covalently linked to a polymer is dispersed in the hydrogel. The complex of formula (IV) follows:

$$(S \ldots P'\!-\!X\!-\!L\!-\!M^{n+})_{gel} \quad (IV)$$

wherein S is a medical device substrate not having functional groups on its surface; P' is a polymer with functional groups X, the polymer not being linked to the surface of the medical device; L is a chelate; M is a paramagnetic ion; n is an integer that is 2 or greater; and subscript "gel" stands for a hydrogel encapsulate.

In a fourth embodiment of the invention, a hydrogel having functional groups can be used instead of a primary polymer. For example, gelatin may be used instead of the polymers discussed above. Accordingly, the gelatin or hydrogel rather than the polymer may be covalently linked with a chelate. The gelatin, e.g., may be covalently linked to a chelate such as DTPA through the lysine groups of gelatin. In addition, hydrogels that are modified to have amine groups in the pendant chains can be used instead of the polymer, and can be linked to chelates using amine groups. The chelate is coordinated with a paramagnetic-metal ion such as Gd(III) as described above with respect to the other embodiments to form a paramagnetic-metal ion/chelate complex, and then mixed with a soluble hydrogel such as gelatin. The soluble hydrogel may be the same or may be different from the hydrogel to which the paramagnetic-metal ion/chelate complex is linked. The resulting mixture is used to coat a substrate or, e.g., a bare polyethylene rod. More particularly, the mixture is used to coat a medical device using the coating techniques described above with respect to the second embodiment. The coated substrate or medical device may then be chill-set. Subsequently, the hydrogel matrix or, for example, the gelatin-gelatin matrix may then be cross-linked with a cross-linker such as glutaraldehyde. The cross-linking results in a hydrogel overcoat, and a substance which is MR-imageable.

Figure 19:
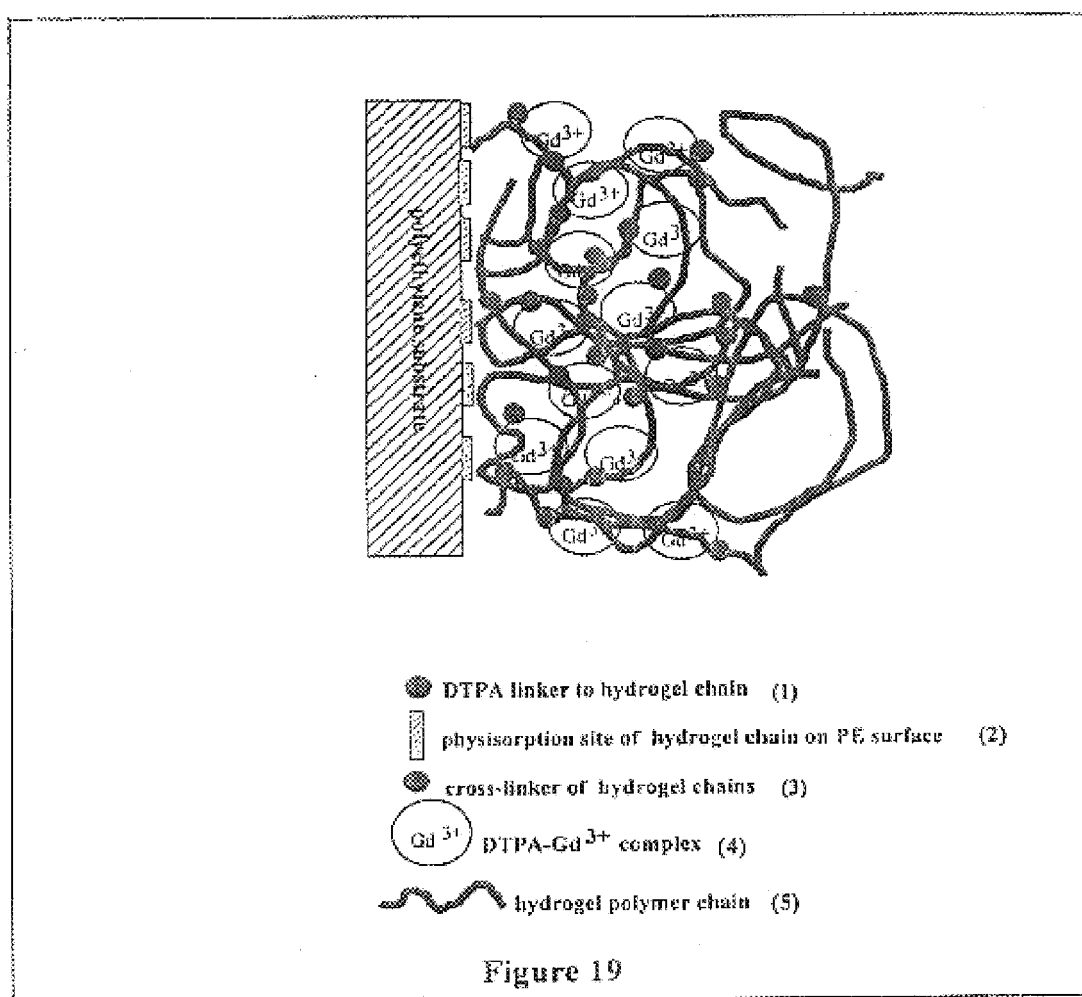
FIG. 19 is a schematic representation of one example of the fourth embodiment of the invention, wherein gelatin is chemically linked with DTPA, which is coordinated with Gd(III) and mixed with soluble gelatin. The resulting mixture of gelatin and DTPA[Gd(III)] complex coats the surface of a medical device, and is then cross-linked with glutaraldehyde to form a hydrogel coat with DTPA[Gd(III)] dispersed therein. In other words.

Example 13 below describes in more detail how one example of the fourth embodiment of the invention can be made. FIG. 19 is a schematic representation of one example of the fourth embodiment of the invention, wherein gelatin is chemically linked with DTPA, which is coordinated with Gd(III) and mixed with free soluble gelatin without any DTPA linked. The resulting mixture of gelatin and DTPA [Gd(III)] complex coats a bare polyethylene surface, and is then cross-linked with glutaraldehyde to form a hydrogel coat with DTPA[Gd(III)] dispersed therein. FIG. 20 shows the chemical details for the example schematically represented in FIG. 19.

The fourth embodiment can be summarized as a coating for visualizing medical devices in magnetic resonance imaging comprising a complex of formula (V). The method includes encapsulating at least a portion of the medical device with a hydrogel, wherein the hydrogel is covalently linked with at least one of the paramagnetic-metal-ion/chelate complexes. The complex of formula (V) follows:

$$(S \ldots G\!-\!X\!-\!L\!-\!M^{n+})gel \quad (V)$$

wherein S is a medical device substrate which is made of any material and does not having any functional groups on its surface; G is a polymer with functional groups X that can also form a hydrogel encapsulate; L is a chelate; M is a paramagnetic ion; n is an integer that is 2 or greater; and subscript "gel" stands for a hydrogel encapsulate.

The present invention is further explained by the following examples which should not be construed by way of limiting the scope of the present invention. A description of the preparation and evaluation of MR-imageable PE polymer rods follows.

EXAMPLES

Example 1

Preparation of Coated Polyethylene Sheets

Polyethylene sheets were coated in the three-step process described herein.

Surface Amination. A polyethylene sheet (4.5 in diameter and 1 mil thick) was placed in a capacitively coupled, 50 kHz, stainless steel plasma reactor (as shown schematically in FIGS. 3 and 3A) and hydrazine plasma treatment of the polyethylene film was performed. The substrate film was placed on the lower electrode. First, the base pressure was established in the reactor. Then, the hydrazine pressure was slowly raised by opening the valve to the liquid hydrazine reservoir. The following plasma conditions were used: base pressure=60 mT; treatment hydrazine pressure=350 mT; RF Power=25 W; treatment time=5 min; source temperature (hydrazine reservoir)=60° C.; temperature of substrate=40° C. Surface atomic composition of untreated and plasma-treated surfaces were evaluated using XPS (Perkin-Elmer Phi-5400; 300 W power; Mg source; 15 kV; 45° takeoff angle).

DTPA Coating. In a 25 mL dry flask, 21.5 mg of DTPA was added to 8 mL of anhydrous pyridine. In a small vessel, 8.9 mg of 1,1'-carbonyldiimidazole (CDI), as a coupling catalyst, was dissolved in 2 mL of anhydrous pyridine. The CDI solution was slowly added into the reaction flask while stirring, and the mixture was stirred at room temperature for 2 hours. The solution was then poured into a dry Petri dish, and the hydrazine-plasma treated polyethylene film was immersed in the solution. The Petri dish was sealed in a desiccator after being purged with dry argon for 10 min. After reaction for 20 hours, the polyethylene film was carefully washed in sequence with pyridine, chloroform, methanol and water. The surface was checked with XPS, and the results showed the presence of carboxyl groups, which demonstrate the presence of DTPA.

Gadolinium (III) Coordination. 0.70 g of $GdCl_3.6H_2O$ was dissolved in 100 mL of water. The DTPA-treated polyethylene film was soaked in the solution for 12 hr. The film was then removed from the solution and washed with water. The surface was checked with XPS and showed two peaks at a binding energy (BE)=153.4 eV and BE=148.0 eV, corresponding to chelated $Gd^{3+}$ and free $Gd^{3+}$, respectively. The film was repeatedly washed with water until the free $Gd^{3+}$ peak at 148.0 eV disappeared from the XPS spectrum.

The results of the treatment in terms of relative surface atomic composition are given below in Table 1.

TABLE 1

| Relative Surface Atomic Composition of untreated and treated PE surfaces | | | | |
|---|---|---|---|---|
| | % Gd | % N | % O | % C |
| Untreated PE | 0.0 | 0.0 | 2.6 | 97.4 |
| Hydrazine plasma treated PE | 0.0 | 15.3 | 14.5 | 70.2 |
| DTPA coated PE | 0.0 | 5.0 | 37.8 | 57.2 |
| Gd coated PE | 1.1 | 3.7 | 35.0 | 60.3 |

Example 2
Preparation of Coated Polyethylene sheets Including Linker Agent

Coated polyethylene sheets were prepared according to the method of Example 1, except that after surface amination, the polyethylene sheet was reacted with a lactam, and the sheet washed before proceeding to the chelation step. The surface of the film was checked for amine groups using XPS.

Example 3
Imaging of Coated Polyethylene and Polypropylene Sheets

Figure 4:
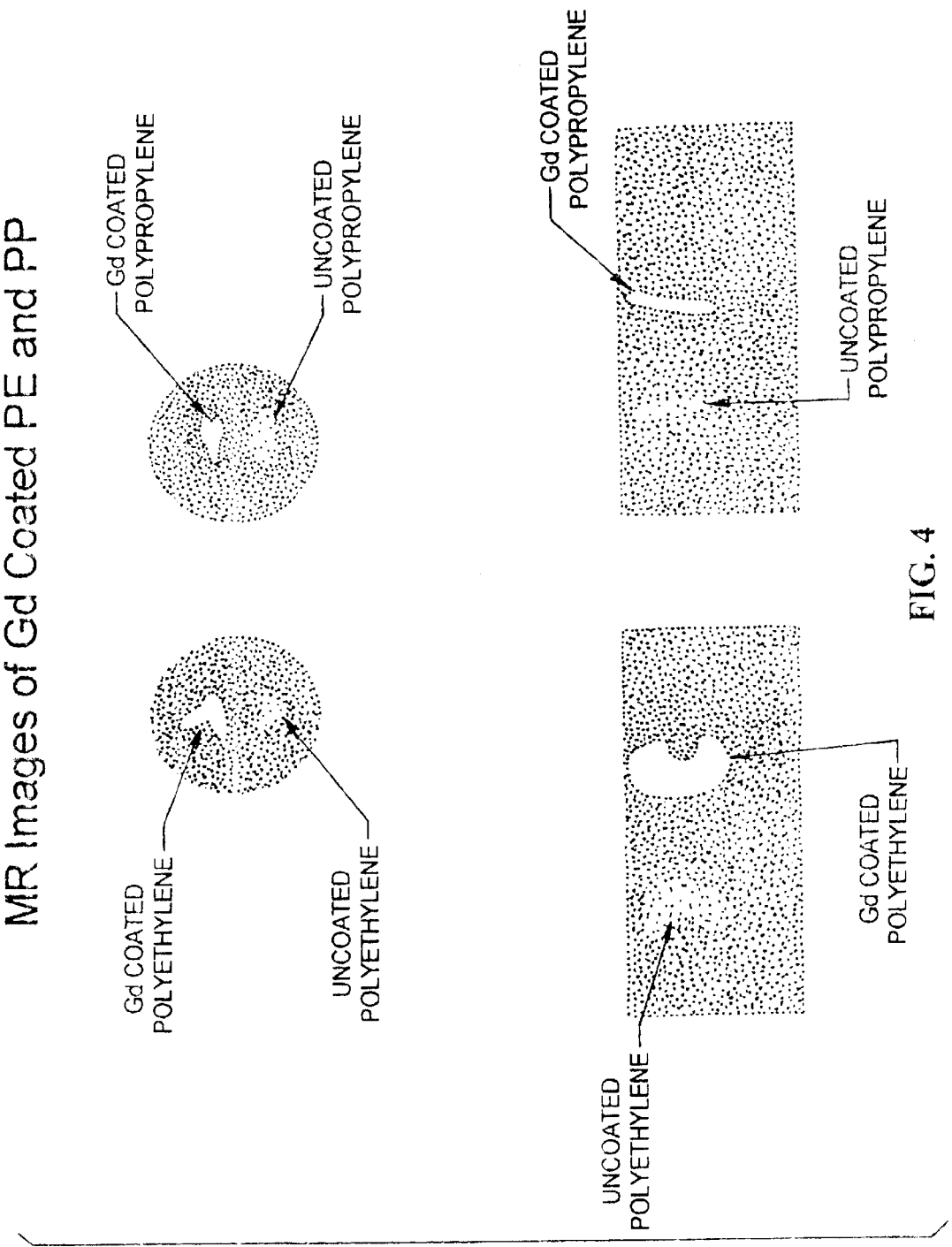
FIG. 4 is several MR images of coated devices in accordance with the present invention.

MR signal enhancement was assessed by imaging coated sheets of polyethylene and polypropylene, prepared as described in Example 1, with gradient-recalled echo (GRE) and spin-echo (SE) techniques on a clinical 1.5 T scanner. The sheets were held stationary in a beaker filled with a tissue-mimic, fat-free food-grade yogurt, and the contrast-enhancement of the coating was calculated by normalizing the signal near the sheet by the yogurt signal. The $T_1$-weighed GRE and SE MR images showed signal enhancement near the coated polymer sheet. The $T_1$ estimates near the coated surface and in the yogurt were 0.4 s and 1.1 s, respectively. No enhancement was observed near control sheets. The MR images acquired are shown in FIG. 4.

Example 4
In Vitro Testing of DTPA[Gd(III)] Filled Catheter Visualization

The following examples demonstrated the utility of DTPA [Gd(III)] in visualizing a catheter under MR guidance.

Figure 5:
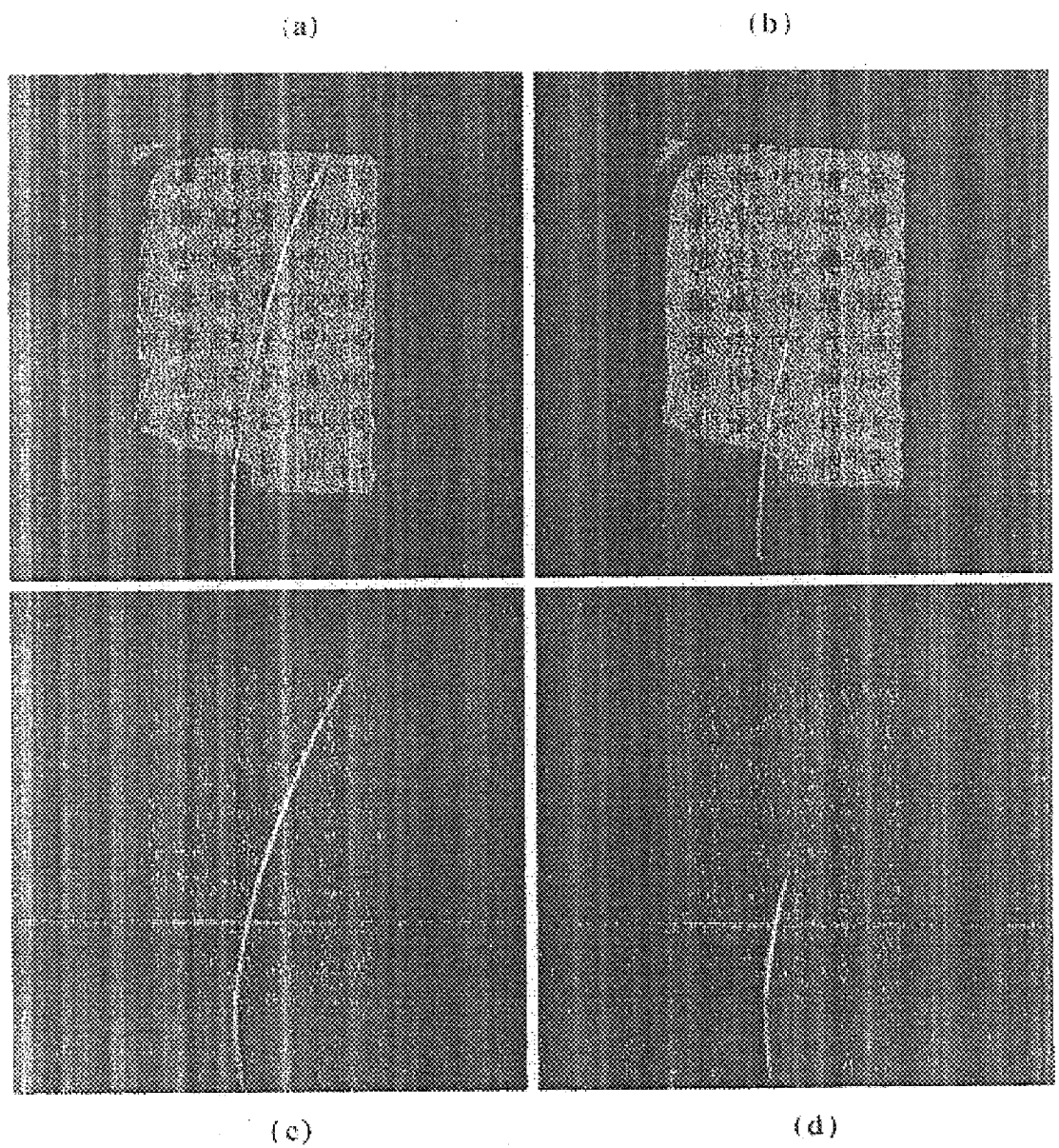
FIG. 5 is temporal MR snapshots of a Gd-DTPA-filled catheter.

A DTPA[Gd(III)] filled single lumen catheter 3–6 French (1–2 mm) was imaged in an acrylic phantom using a conventional MR Scanner (1.5T Signa, General Electric Medical Systems) while it was moved manually by discrete intervals over a predetermined distance in either the readout direction or the phase encoding direction. The phantom consisted of a block of acrylic into which a series of channels had been drilled. The setup permitted determination of the tip position of the catheter with an accuracy of ±1 mm (root-mean-square). Snapshots of the catheter are shown in FIG. 5.

Example 5
In Vivo Testing of DTPA[Gd(III)] Filled Catheter Visualization

Figure 6:
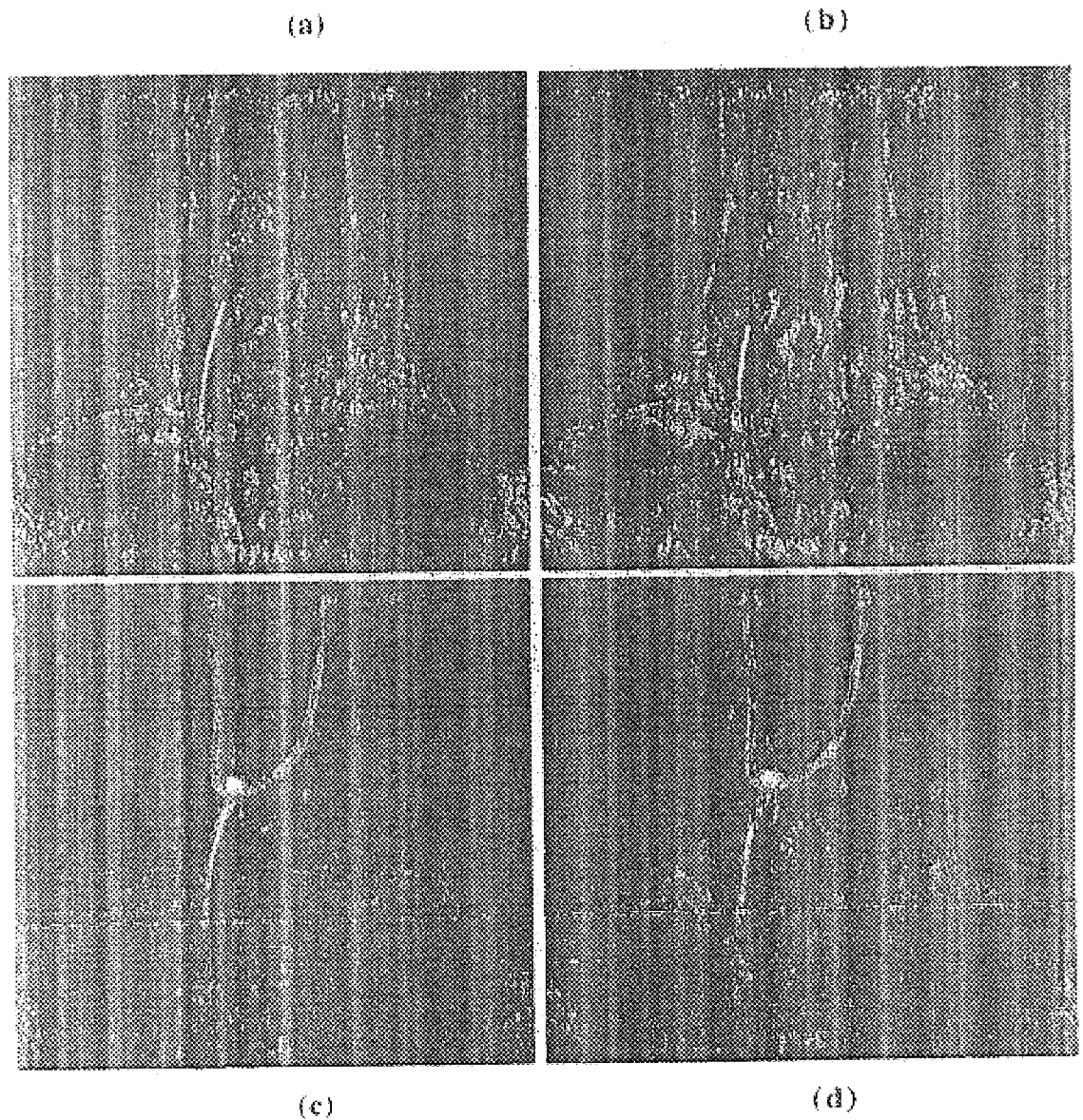
FIG. 6 is temporal MR snapshots of a Gd-DTPA-filled catheter moving in the common carotid of a canine.
Figure 7:
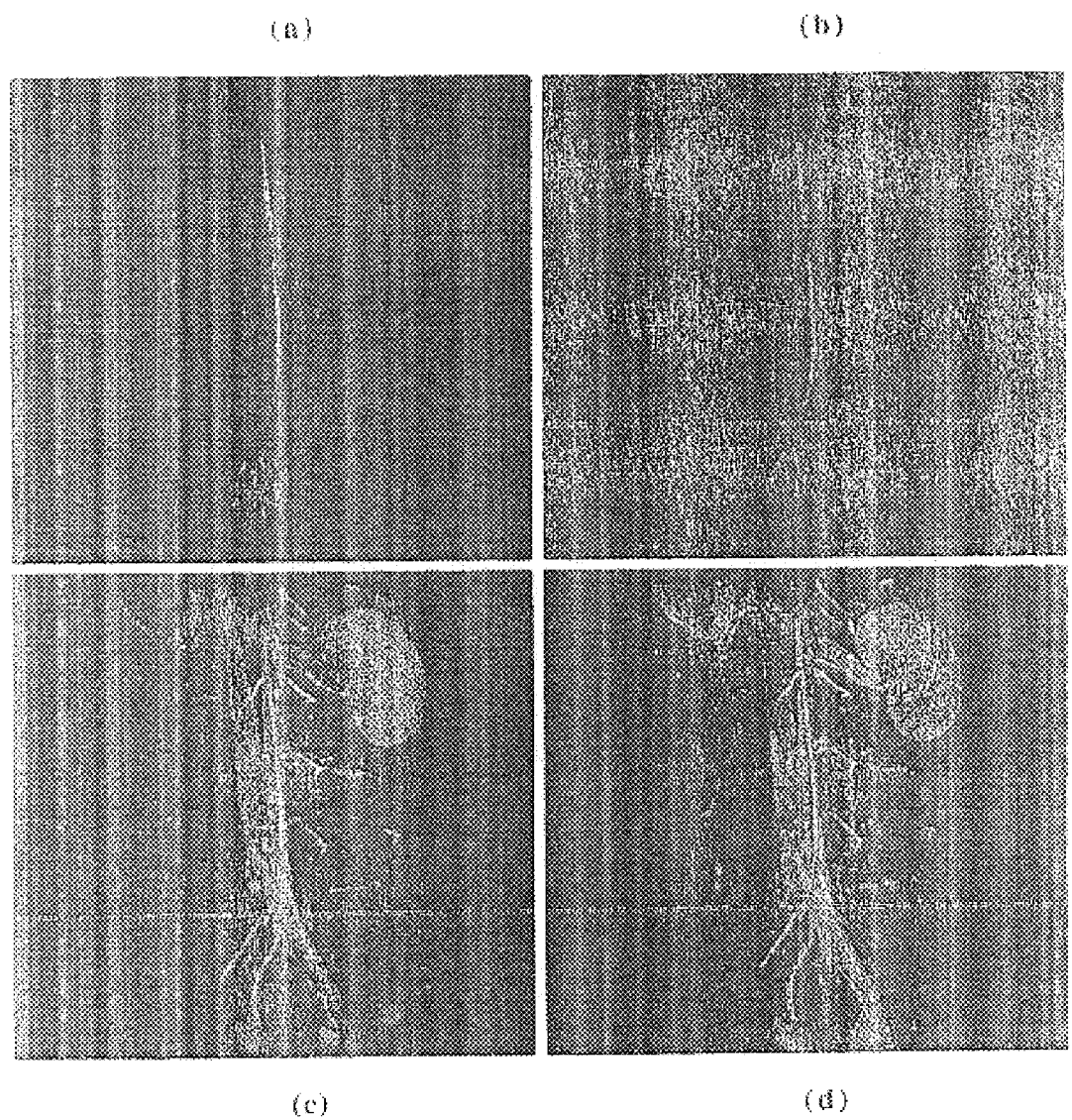
FIG. 7 is temporal MR snapshots of a Gd-DTPA-filled catheter in a canine aorta.

For in vivo evaluation, commercially-available single lumen catheters filled with DTPA[Gd(III)] (4–6% solution), ranging in size between 3 and 6 French (1–2 mm), and catheter/guide-wire combinations were imaged either in the aorta or in the carotid artery of four canines. All animal experiments were conducted in conjunction with institution-approved protocols and were carried out with the animals under general anesthesia. The lumen of the catheter is open at one end and closed at the other end by a stopcock. This keeps the DTPA[Gd(III)] solution in the catheter. The possibility of DTPA[Gd(III)] leaking out of the catheter lumen through the open end was small and is considered safe because the DTPA[Gd(III)] used in these experiments is commercially available and approved for use in MR. Reconstructed images made during catheter tracking were superimposed on previously acquired angiographic "roadmap" images typically acquired using a 3D TRICKS imaging sequence (F. R. Korosec, R. Frayne, T. M. Grist, C. A. Mistretta, *Magn. Reson. Medicine*. 1996, 36 345–351, incorporated herein by reference) in conjunction with either an intravenous or intra-arterial injection of DTPA[Gd(III)] (0.1 mmol/kg). On some occasions, subtraction techniques were used to eliminate the background signal from the catheter images prior to superimposing them onto a roadmap image. Snapshots of the canine carotids and aortas are shown in FIGS. 6 and 7, respectively.

Example 6
In Vivo Catheter MR Visualization

Using canines, a catheter coated with a coating in accordance with the present invention/guide-wire combination is initially positioned in the femoral artery. Under MR guidance, the catheter is moved first to the aorta, then to the carotid artery, then to the circle of Willis, and on to the middle cerebral artery. The catheter movement is clearly seen in the vessels. The length of time to perform this procedure and the smallest vessel successfully negotiated is recorded.

Example 7
Paramagnetic Ion Safety Testing

A gadolinium leaching test is performed to ascertain the stability of the DTPA[Gd(III)] complex. Polyethylene sheets coated with a coating in accordance with the present invention are subjected to simulated blood plasma buffers and blood plasma itself. NMR scans are taken and distinguish between chelated $Gd^{3+}$ and free $Gd^{3+}$. The results indicate that the $Gd^{3+}$ complex is stable under simulated blood conditions.

Example 8
Biocompatibility Testing

A biocompatibility test, formulated as non-specific binding of serum proteins, is carried out on polymeric surfaces coated in accordance with the present invention using an adsorption method of serum albumin labeled with fluorescent dyes. If the albumin is irreversibly adsorbed as detected by fluorescence of coated catheter surfaces, the coat is adjudged to be not biocompatible.

Example 9
Determination of Coating Signal Intensities

A clinical 1.5 T scanner (Signa, General Electric Medical Systems) is used to determine the optimal range of coating densities (in mmol $Gd^{3+}/m^2$) for producing appreciable signal enhancement on a series of silicon wafers coated with a polyethylene-Gd-containing coating in accordance with the present invention. The wafers are placed in a water bath and scanned cross-sectionally using a moderately high-resolution fast gradient-recalled echo (FGRE) sequence with TR≈7.5 ms/TE≈1.5 ms, 256×256 acquisition matrix and a 16 cm×16 cm field-of-view (FOV). The flip angle is varied from 10° to 90° in 10° increments for each coating density. A region of interest (ROI) is placed in the water adjacent to the wafer and the absolute signal is calculated.

For calibration of signal measurements obtained in different imaging experiments, a series of ten calibration vials is also imaged. The vials contain various concentrations of DTPA[Gd(III)], ranging from 0 mmol/mL to 0.5 mmol/mL. This range of concentrations corresponds to a range of $T_1$ relaxation times (from <10 ms to 1000 ms) and a range of $T_2$ relaxation times. The signals in each vial are also measured and used to normalize the signals obtained near the wafers. Normalization corrections for effects due to different prescan settings between acquisitions and variable image scaling are applied by the scanner. A range of concentrations in the vials facilitates piece-wise normalization. An optimal range of coating densities is determined.

Example 10
Comparison Testing of MR-imageability of Three Differently coated Samples Because many medical devices are made of polyethylene (PE), PE rods were used in a variety of tests in order to mimic the surface of a catheter or medical device. In this specific example (as fully set forth in the preparation of Sample 2), the PE rods (2 mm diameter) were functionalized or precoated with a hydrophilic polymer containing primary amine groups. Through amide linkage, diethylenetrimaminepentaacetic acid (DTPA) was covalently attached to the rods. Subsequently, Gd(III) was complexed to the DTPA. The necessary contrast for MRI is the result of interactions of proton of water in body fluid (e.g., blood) with the highly magnetic Gd(III) ion, and the resulting shortening of $T_1$ relaxation time of the water protons. To reduce the mobility of the DTPA[Gd(III)] complex for imaging in accordance with the present invention agarose gel was used to encapsulate the entire assembly. Such a rod was used as Sample 2 in the testing as further described below.

To test the effectiveness of agarose gel in reducing the mobility of the DTPA[Gd(III)] complex, and accordingly, enhancing the MR-imageability of the medical device, two other samples were tested in parallel. Sample 1 was a blank sample, i.e. a PE rod encapsulated with agarose gel but having no DTPA[Gd(III)] complexed to the rod; Sample 3 was a PE rod encapsulated with agarose gel containing a DTPA[Gd(III)] complex, but the complex was not covalently linked to the PE rods. MRI tests were carried out in three media: 1) a fat-free food-grade yogurt (a tissue mimic); 2) a physiological saline (a serum mimic); and 3) human blood. In summary, the following three agarose-encapsulated samples were tested in each media: the blank sample having no DTPA[Gd(III)] complex, but encapsulated in agarose (Sample 1); the chemically-bound or covalently linked DTPA[Gd(III)] complex encapsulated in agarose (Sample 2); and the unbound DPTA[Gd(III)] encapsulated in agarose (Sample 3). Sample 1, the blank, gave no detectable MRI signal. Sample 2 gave clearly detectable signals up to ten hours. Sample 3 lost signal intensity with time, thereby indicating a slow leaching of DTPA[Gd(III)] complex from the agarose gel matrix because it was not covalently bound to the polymer of the medical device. Given the observed MR images of Samples 2 and 3, the agarose encapsulation is adjudged to be optimal.

Specific preparation and evaluation of MR-imageable PE polymer rods is as follows.

Preparation of Sample 1

Sample 1 was prepared by coating blank PE rods with agarose gel. The PE rods for Sample 1 and all samples were obtained from SurModics, Inc. located at 9924 West 74th Street, Eden Prairie, Minn. 55344-3523. Agarose (type VI-A) was purchased from Sigma located in St. Louis, Mo., with gel point (1.5% gel) at 41.0°±1.5° C., gel strength (1.5%) expressed in units of elastic modulus larger than 1200 g/cm², and melting temperature 95.0°±1.5° C. 0.60 g agarose was dissolved in 40 mL distilled water in a flask maintained at 100° C. for 5 min. The solution was kept in a water bath at 50–60° C. The PE rods were then dipped into the agarose solution. After removing the rods from the solution, the rods were cooled to room temperature in order to allow a gel-coating to form on the rod surface. The same procedure was repeated to overcoat additional layers of agarose, and it was repeated for 5 times for each rod. Thus, all rods were expected to have about the same gel-coating thickness.

Preparation of Sample 2

Polyethylene (PE) rods with an amine-containing-polymer coating were provided by SurModics, Inc. SurModics, Inc. functionalizes the PE surface of the rods by a photochemical attachment of poly(2-aminoethyl methacrylate) in order to provide functional groups, more specifically, amine groups, on the functionalized surface of the rods. Again, the PE rods in the example were meant to mimic the surface of existing medical devices made from a wide variety of polymers. Diethylenetriaminepentaacetic acid (DTPA), gadolinium trichloride hexahydrate, $GdCl_3.6H_2O$ (99.9%), dicyclohexylcarbodiimide (DCC), and 4-(dimethylamino)-pyridine (DMAP) were all purchased from Aldrich located at Milwaukee, Wis., and used without further purification. Agarose (type VI-A) was purchased from Sigma located at St. Louis, Mo., with gel point (1.5% gel) at 41.0°±1.5° C., gel strength (1.5%) larger than 1200 g/cm², and melting temperature 95.0°±1.5° C. Human blood used in the MRI experiments were obtained from the University of Wisconsin Clinical Science Center Blood Bank located in Madison, Wis.

Figure 8:
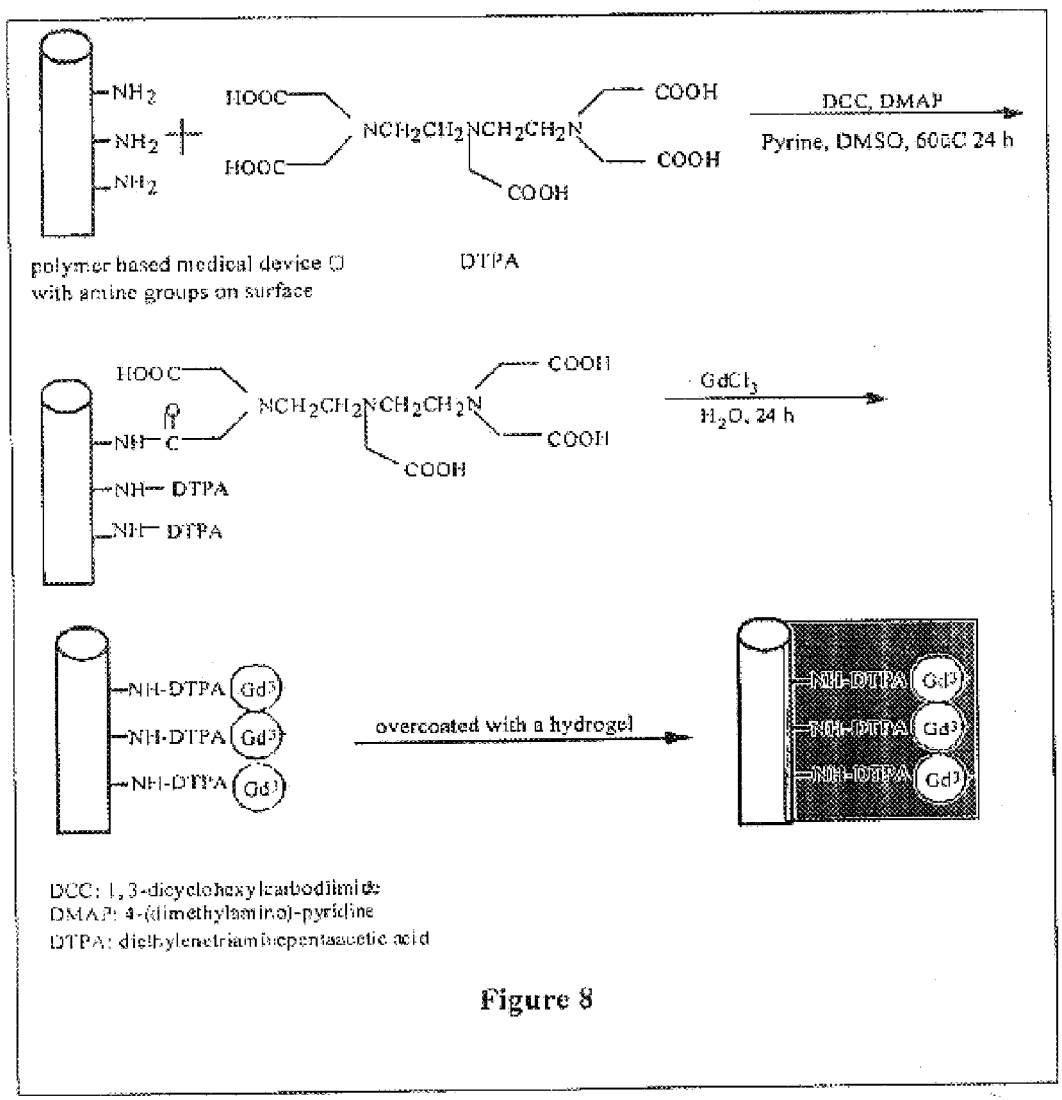
FIG. 8 is a schematic showing one example of a chemical synthesis of the present invention by which an existing medical device can be made MR-imageable. More particularly.

The MRI-signal-emitting coatings were prepared on the PE rods, i.e. the pre-existing rods were made MR-imageable, by the chemical synthesis depicted in FIG. 8. The individual steps of the chemical synthesis are explained in detail below.

To attach the DTPA (i.e. chelate) to the PE rods by amide linkage, 0.165 g DTPA (0.42 mmol) was dissolved in 30 mL of 1:1 (by volume) mixture of pyridine and DMSO in a flask and stirred at 80° C for 30 min. Subsequently, 5-cm long PE rods having the amine-containing-polymer coating were immersed in the solution. After stirring for 2 hours at room temperature, 0.090 g DCC (0.43 mmol) and 0.050 g DMAP (0.41 mmol) solution in pyridine (4 mL) was slowly added to the solution while stirring. Then the reaction mixture was kept in an oil bath at 60° C. for 24 hours while stirring. Subsequently, the PE rods were removed from the solution and washed three times—first with DMSO and then with methanol, respectively.

To complex or coordinate Gd(III) with the DTPA, now linked to the PE rods, 0.140 g $GdCl_3.6H_2O$ (0.38 mmol) was dissolved in 15 mL of distilled water in a test tube. The DTPA-linked-PE rods were soaked in this solution at room temperature for 24 hours while stirring. The rods were then washed with distilled water several times and soaked in distilled water for an additional hour to remove any residual $GdCl_3$.

To encapsulate the PE rods in the final step of the chemical synthesis as shown in FIG. 8, 0.60 g agarose was dissolved in 40 mL distilled water in a flask maintained at 100° C. for 5 min. The agarose solution so obtained was then kept in a water bath at 50–60° C. The DTPA[Gd(III)] linked rods were then dipped into the agarose solution. After removing the rods from the agarose solution, the rods were cooled down to room temperature in order to allow for encapsulation, i.e., to allow the gel coating to cover the rod surface. The same procedure was repeated 5 times to coat additional layers of agarose gel on the rods. Thus, all rods, having undergone the same procedure, were expected to have about the same gel-coating thickness.

Preparation of Sample 3

Sample 3 was prepared by coating PE rods with agarose gel and a DTPA[Gd(III)] mixture. 0.45 g agarose (also obtained from Sigma) was dissolved in 30 mL distilled water in a flask maintained at 100° C. for 5 min. Then, 3 mL of 0.4% solution of DTPA[Gd(III)] was added to the agarose solution. The solution was kept in a water bath at 50–60° C. The rods were dipped into the agarose solution, and then were removed. The adsorbed solution on the rod was cooled to room temperature to allow a gel-coating to form. The same procedure was repeated to coat additional layers of agarose, and it was repeated for 5 times altogether for each rod. Thus, all rods were expected to have about the same gel coating thickness. Sample 3 differed from Sample 2 in that the DTPA[Gd(III)] complex was not covalently bonded to the PE rod using the methods of the present invention. Instead, a DTPA[Gd(III)] mixture was merely added to the agarose solution, resulting in dispersion of the same in the gel upon encapsulation in 5-layer coating.

Testing

The samples were then subjected to characterization by x-ray photoelectron spectroscopy (XPS) and magnetic resonance (MR) measurements. XPS measurements were performed with a Perkin-Elmer Phi 5400 apparatus. Non-monochromatized $MgK_\alpha$ X-ray has been utilized at 15W and 20mA, and photoelectrons were detected at a take-off angle of 45°. The survey spectra were run in the binding energy range 0–1000 eV, followed by high-resolution spectra of C(1s), N(1s), O(1s) and Gd(4d).

MR evaluation of the signal-emitting rods was performed on a clinical 1.5T scanner. The PE rods were each imaged in the following medium: 1) yogurt as a suitable tissue mimic; 2) saline as an electrolyte mimic of blood serum; and 3) and human blood. Spin echo (SE) and RF spoiled gradient-recalled echo (SPGR) sequences were used to acquire images.

Results

The surface chemical composition of the rods was determined by the XPS technique. Table 2, below, lists the relative surface atomic composition of the untreated rods as provided by SurModics (Eden Prairie, Minn.). Table 3 shows the relative surface composition of the treated (DTPA [Gd(III)] linked) rods. After the chemical treatment outlined in FIG. 8, the relative composition of oxygen increased from 10.8% to 25.9% as seen in Tables 2 and 3. This indicates that DTPA is indeed attached to the polymer surface. Furthermore, it is clear that Gd(III) was complexed to the DTPA on the polymer surface, thus giving rise to the surface Gd composition of 3.2%.

TABLE 2

Surface compositions in % of 3 elements, C, N and O, of PE rods coated with the $NH_2$-containing polymer (SurModics).

| Location | C(1s) | N(1s) | O(1s) |
|---|---|---|---|
| 1 | 80.7 | 8.6 | 10.7 |
| 2 | 80.2 | 8.3 | 11.5 |
| 3 | 80.4 | 9.3 | 10.3 |
| average | 80.4 (±0.3) | 8.7 (±0.5) | 10.8 (±0.6) |

TABLE 3

Surface composition in % of 4 elements of the PE rods linked with DTPA[Gd(III)]

| Location | C(1s) | N(1s) | O(1s) | Gd(4d) |
|---|---|---|---|---|
| 1 | 65.2 | 5.8 | 25.9 | 3.1 |
| 2 | 63.2 | 7.2 | 26.5 | 3.1 |
| 3 | 63.6 | 7.8 | 25.2 | 3.3 |
| average | 64.0 (±1.0) | 6.9 (±1.0) | 25.9 (±0.7) | 3.2 (±0.1) |

Figure 9:
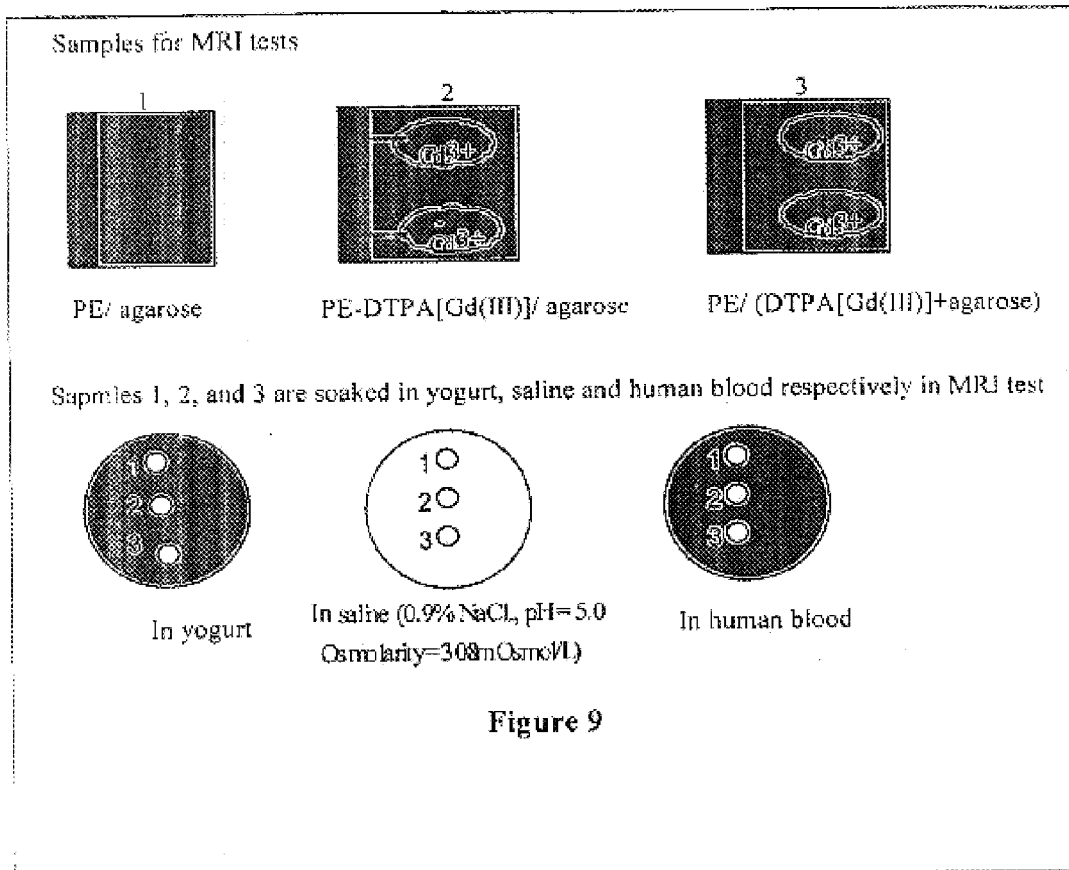
FIG. 9 is a diagram showing hydrogel encapsulation of three samples to undergo MR-imageability testing.

The polymer rods linked with DTPA[Gd(III)] and encapsulated by agarose gel (Sample 2) were imaged in yogurt, saline and human blood. At the same time, the control rods, i.e., the PE rods having no chemical treatment but having only the gel overcoat (Sample 1) as well as PE rods coated with the gel in which DTPA[Gd(III)] is dispersed but not covalently linked (Sample 3) were also imaged in yogurt, saline and blood using spin echo (SE) and RF spoiled gradient-recalled echo (SPGR) sequences. Typical scan parameters for 2D SE sequence were: TR=300 ms, TE=9 ms, acquisition matrix=256×256, FOV=20 cm×20 cm, slice thickness=3 mm, flip angle=30°. Typical scan parameters for 3D SPGR sequence were: TR=18 ms, TE=3.7 ms. acquisition matrix=256×256, FOV=20 cm×20 cm, slice thickness=3 mm, flip angle=30°. The three kinds of samples and the MRI imaging set-up are illustrated in FIG. 9.

Figure 10:
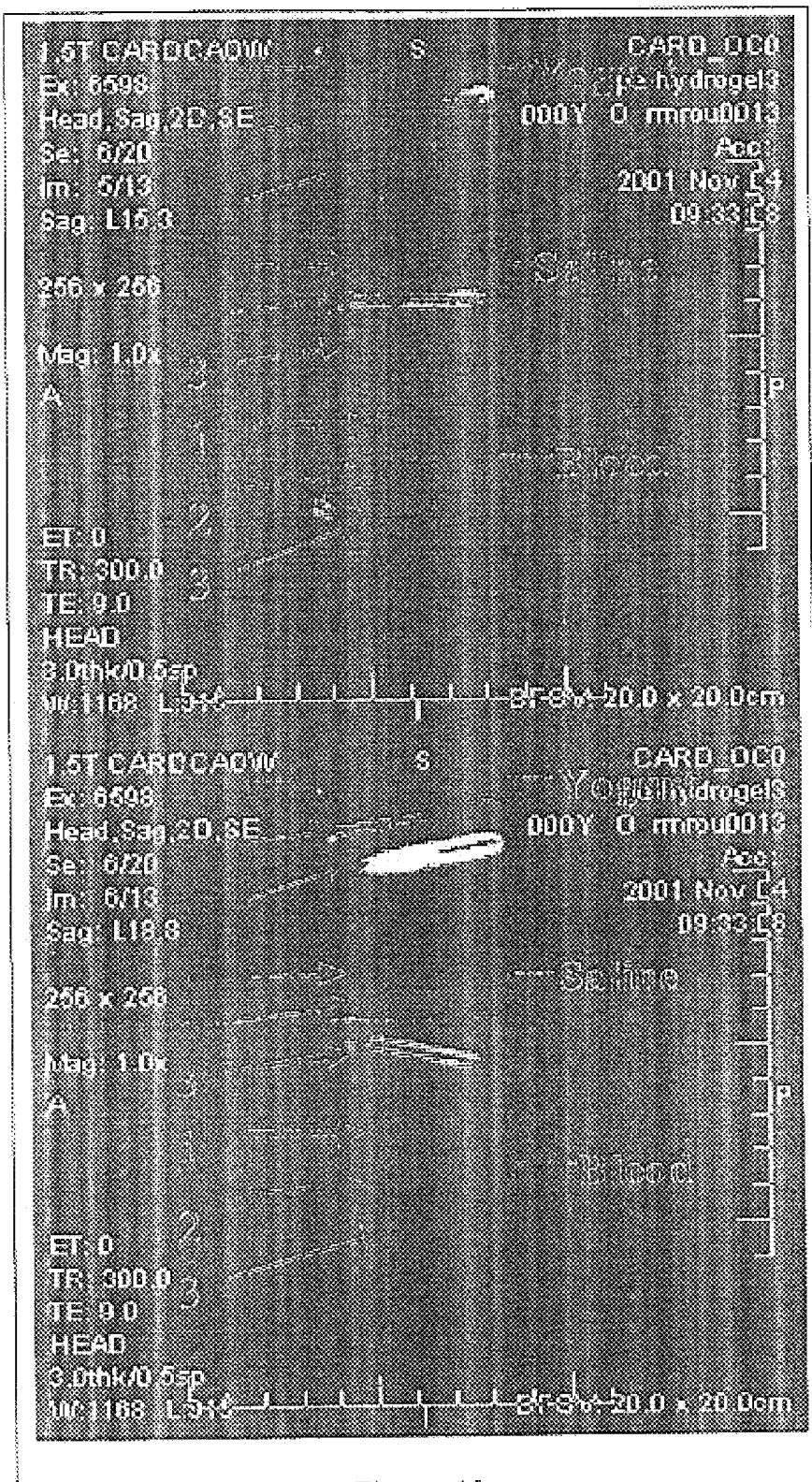
FIG. 10 is a temporal MR snapshot showing the MR-imageability of three samples in three different media (namely yogurt, saline and blood) after being introduced therein for 15+ minutes, wherein 1 is polyethylene ("PE")/agarose; 2 is PE-DTPA[Gd(III)]/agarose; and 3 is PE/(DTPA [Gd(III)+agarose) in yogurt, saline, and blood 15 minutes later. The upper and lower frames represent different slices of the same image.
Figure 11:
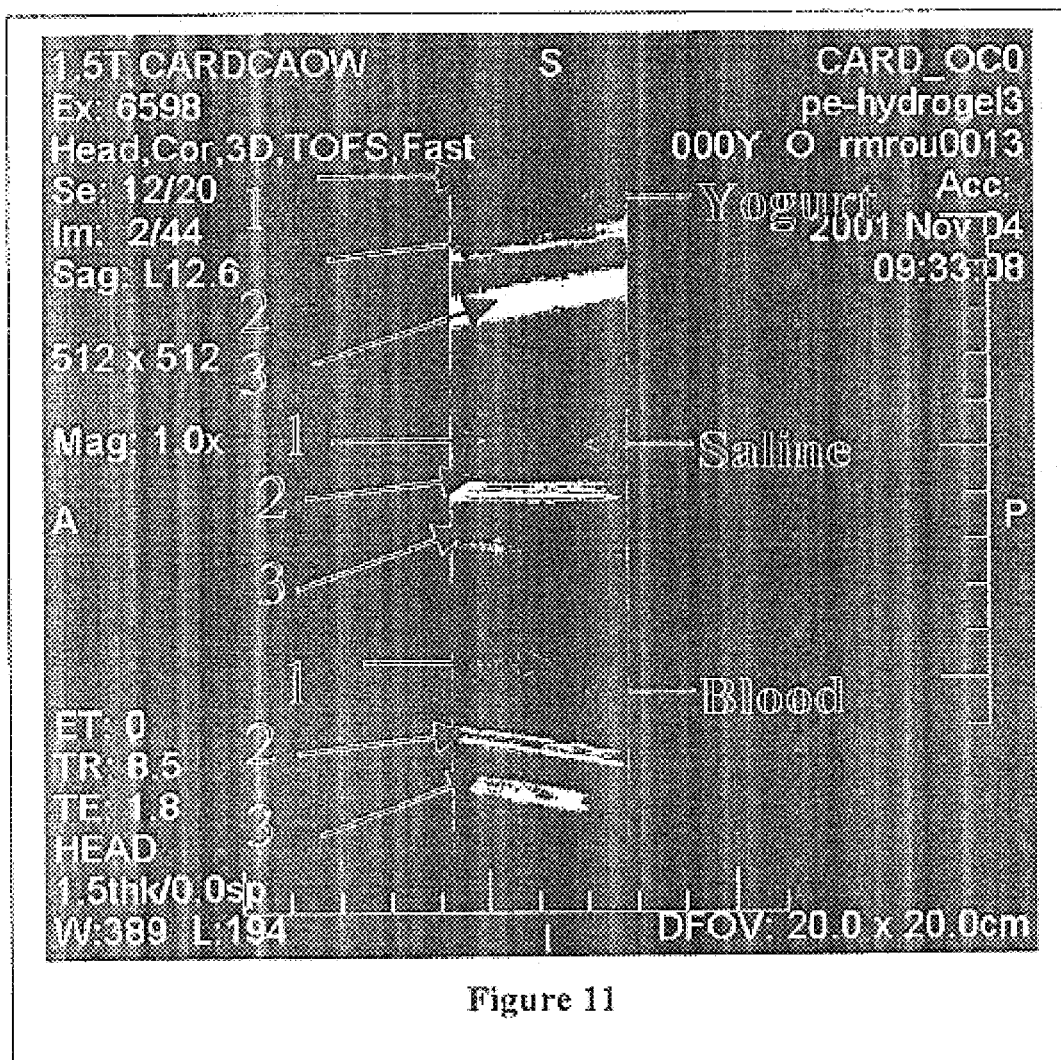
FIG. 11 is a temporal MR snapshot showing the MR-imageability of three samples in three different media (namely yogurt, saline and blood) after being introduced therein for 60+ minutes, wherein 1 is PE/agarose; 2 is PE-DTPA[Gd(III)]/agarose; and 3 is PE/(DTPA[Gd(III)+agarose); in yogurt, saline, and blood 60+ minutes later.
Figure 12:
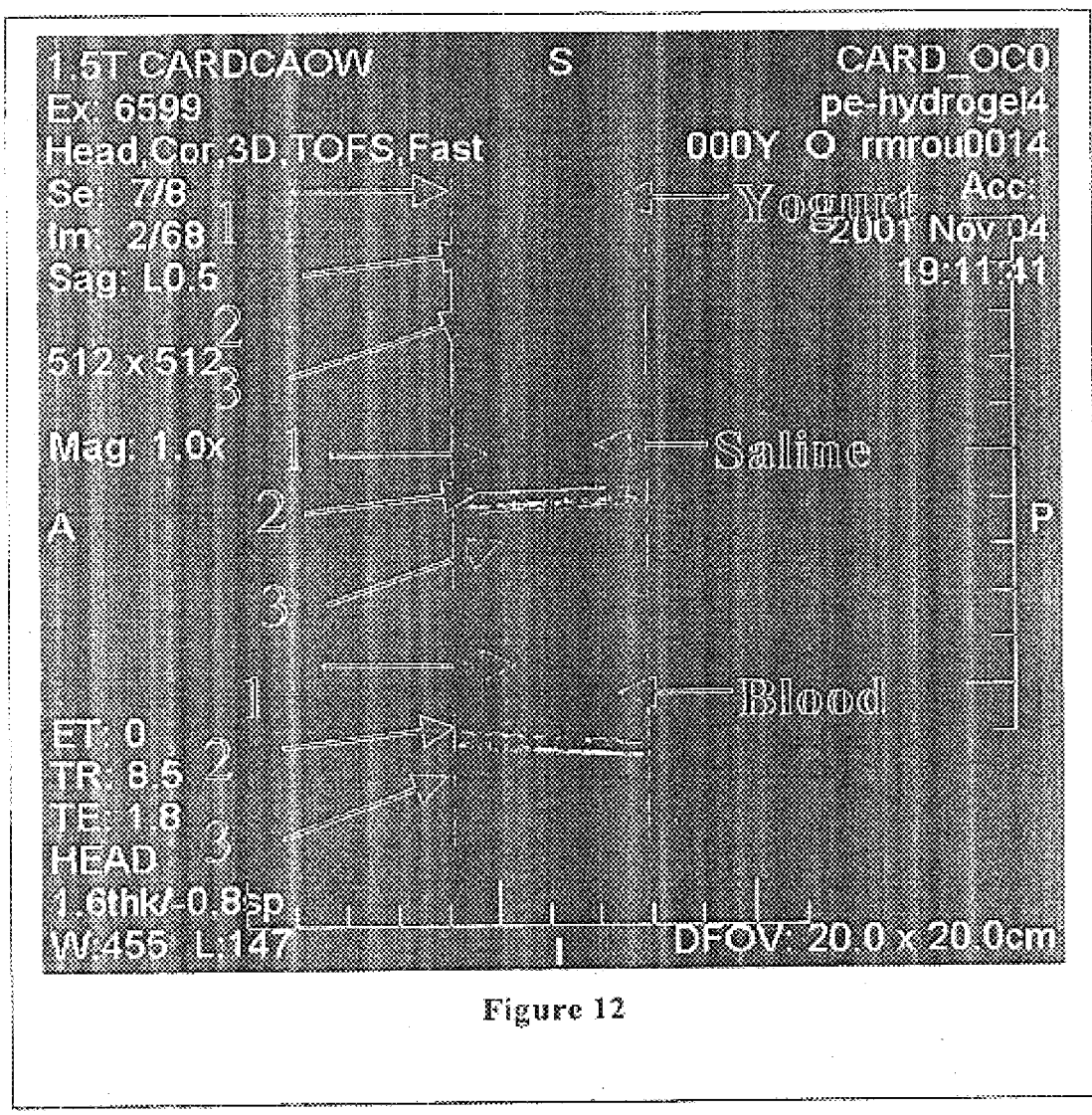
FIG. 12 is a temporal MR snapshot showing the MR-imageability in a longitudinal configuration of three samples in three different media (namely yogurt, saline and blood) after being introduced therein for 10+ hours, wherein 1 is PE/agarose; 2 is PE-DTPA[Gd(III)]/agarose; and 3 is PE/(DTPA[Gd(III)+agarose); in yogurt, saline, and blood 10+ hours later.

The rods were imaged, the results of which are shown in FIGS. 10–12. More particularly, FIG. 10 shows the longitudinal MR image of each sample in each medium after 15+ minutes; FIG. 11 shows the longitudinal MR images after 60+ minutes; and FIG. 12 shows the longitudinal MR images of each sample in each medium after 10+ hours. As these figures illustrate, Sample 1 (i.e. PE rods coated only with the gel and without DTPA[Gd(III)]) is not visible in all three media, yogurt, saline, or blood. Sample 2 (i.e. PE rods covalently-linked with DTPA[Gd(III)] with overcoats of the gel) is visible in yogurt, saline, and blood and was clearly visible even after 10 hours as shown in FIG. 12. Sample 3 is also visible in yogurt, saline, and blood; however, DTPA [Gd(III)] appears to leach and diffuse out of the gel overcoat with time because it is not covalently bonded to the polymer rod. For example, after 10 hours, sample 3 is not visible in saline or blood.

The summary of the MR experiments is presented in Table 4. Consequently, Sample 2 having DTPA[Gd(III)] covalently linked to polyethylene) exhibits better MR-imageability for longer periods of time compared to Sample 1 and Sample 3. In addition, it appears that encapsulating rods or medical devices having the paramagnetic-metal-ion/chelate complex covalently linked thereto with a hydrogel improves or enhances the MR-imageability thereof. In Table 4, a "+" indicates that the sample was visible, while "−" indicates that the sample was not visible.

TABLE 4

MR signals of the samples in yogurt, saline and blood.

| Time | | 20 mins | 2 hours | 10 hours | 10 hours and replace the yogurt and blood |
|---|---|---|---|---|---|
| In yogurt | 1 | − | − | − | − |
| | 2 | + | + | + | + |
| | 3 | + | +, but the | +, but the | + |

TABLE 4-continued

MR signals of the samples in yogurt, saline and blood.

| Time | | 20 mins | 2 hours | 10 hours | 10 hours and replace the yogurt and blood |
|---|---|---|---|---|---|
| | | | signal diffused and became bigger | signal diffused much | |
| In saline | 1 | – | – | – | – |
| | 2 | + | + | +, and the signal as strong as that of 20 mins | +, and the signal as strong as that of 20 mins |
| | 3 | + | +, but decreased | – | – |
| In blood | 1 | – | – | – | – |
| | 2 | + | + | + | + |
| | 3 | + | +, but decreased | – | – |

Example 11
Attaching DTPA to PE Rods via Amide Linkage; Complexing Gd (III) with DTPA Linked PE Rods; Gelatin Encapsulating on DTPA[Gd(III)] Attached PE Rods; and Cross-linking the Gel-coating on PE Rods. The Schematic Structure of the Coating and Chemistry Detail are Illustrated in FIGS. 13 and 14.

Diethylenetriaminepentaacetic acid (DTPA), gadolinium trichloride hexahydrate, $GdCl_3 \cdot 6H_2O$ (99.9%), dicyclohexylcarbodiimide (DCC), 4-(dimethylamino)-pyridine (DMAP), dimethyl sulfoxide(DMSO), and pyridine were all purchased from Aldrich, Milwaukee, Wis., and used without further purification. Gelatin type (IV) was provided by Eastman Kodak Company as a gift. Glutaraldehyde(25% solution) was purchased from Sigma, St. Louis, Mo. These materials were used in Example 11, as well as Examples 12–13.

Attachment of DTPA on PE Rods via Amide Linkage 0.165 g DTPA (0.42 mmol) was dissolved in 30 mL of 2:1 (by volume) mixture of pyridine and DMSO in a flask and stirred at 80° C. for 30 min. Then, a 40-cm long polyethylene (PE) rod (diameter 2 mm) with the amine containing polymer precoating were immersed in the solution. The PE rods with an amine-containing-polymer coating were provided by SurModics, Inc. SurModics, Inc. functionalizes the PE surface of the rods by a photochemical attachment of poly(2-aminoethyl methacrylate) in order to provide functional groups, more specifically, amino groups, on the functionalized surface of the rods. Again, the PE rods were meant to mimic the surface of existing medical devices made from a wide variety of polymers. After stirring for 2 hours at room temperature, a pyridine solution (4 mL) containing amidation catalysts, 0.090 g DCC (0.43 mmol) and 0.050 g DMAP (0.41 mmol), was slowly added to the PE rod soaked solution with stirring. Subsequently, the reaction mixture was kept in an oil bath at 60° C. for 24 hours with stirring to complete the bonding of DTPA to the amine groups on the precoated polymer via amide linkage. Subsequently, the PE rods were removed from the solution and washed three times first with DMSO and then with methanol.

Complexation of Gd (III) with DTPA Linked PE Rods 0.50 g $GdCl_3 \cdot 6H_2O$ (0.38 mmol) was dissolved in 100 mL distilled water in a test tube. The DTPA linked PE rods (40-cm long) were soaked in the solution at room temperature for 24 hours while stirring, then the rods were washed with distilled water several times to remove the residual $GdCl_3$.

Gelatin Coating on DTPA[Gd(III)] Attached PE Rods

A sample of gelatin weighing 20 g was dissolved in 100 mL of distilled water at 60° C. for 1 hour with stirring. The solution was transferred to a long glass tube with a jacket and kept the water bath through the jacket at 35° C. DTPA[Gd(III)] attached PE rods (40-cm long) were then dipped into the solution, and the rods upon removing from the solution were cooled to room temperature in order to allow a gel-coating to chill-set, i.e., to form as a hydrogel coating on the rod surface. The final dry thickness of gel-coating was around 30 μm. The same procedure may be repeated to overcoat additional layers of the gel. When it was repeated twice, the final dry thickness of gel-coating was around 60 μm.

Cross-linking of the Gel-coating on PE Rods

Several minutes after the gel-coating, the coated PE rods was soaked in 0.5% glutaraldehyde 300 mL for 2 hours to cross-link the gelatin coating. Then the rods were washed by distilled water and further soaked in distilled water for one hour to remove any residual free glutaraldehyde and $GdCl_3$. Finally the gel-coated rods were dried in air.

Results

The surface chemical composition of the rods was determined by the XPS technique. The results are similar to that in Example 10. After the chemical treatment, DTPA is indeed attached to the polymer surface and Gd(III) was complexed to the DTPA on the polymer surface with the surface Gd composition around 3%.

The polymer rods linked with DTPA[Gd(III)] and encapsulated by cross-linked gelatin imaged in a canine aorta using 2D and 3D RF spoiled gradient-recalled echo (SPGR) sequences. Typical scan parameters for 2D SPGR sequence were: TR=18 ms, TE=3.7 ms. acquisition matrix=256×256, FOV=20 cm×20 cm, slice thickness=3 mm, and flip angle= 30°. Typical scan parameters for 3D SPGR sequence were: TR=8.8 ms, TE=1.8 ms. acquisition matrix=512×192, FOV=20 cm×20 cm, slice thickness=2 mm, and flip angle= 60°.

Figure 15:
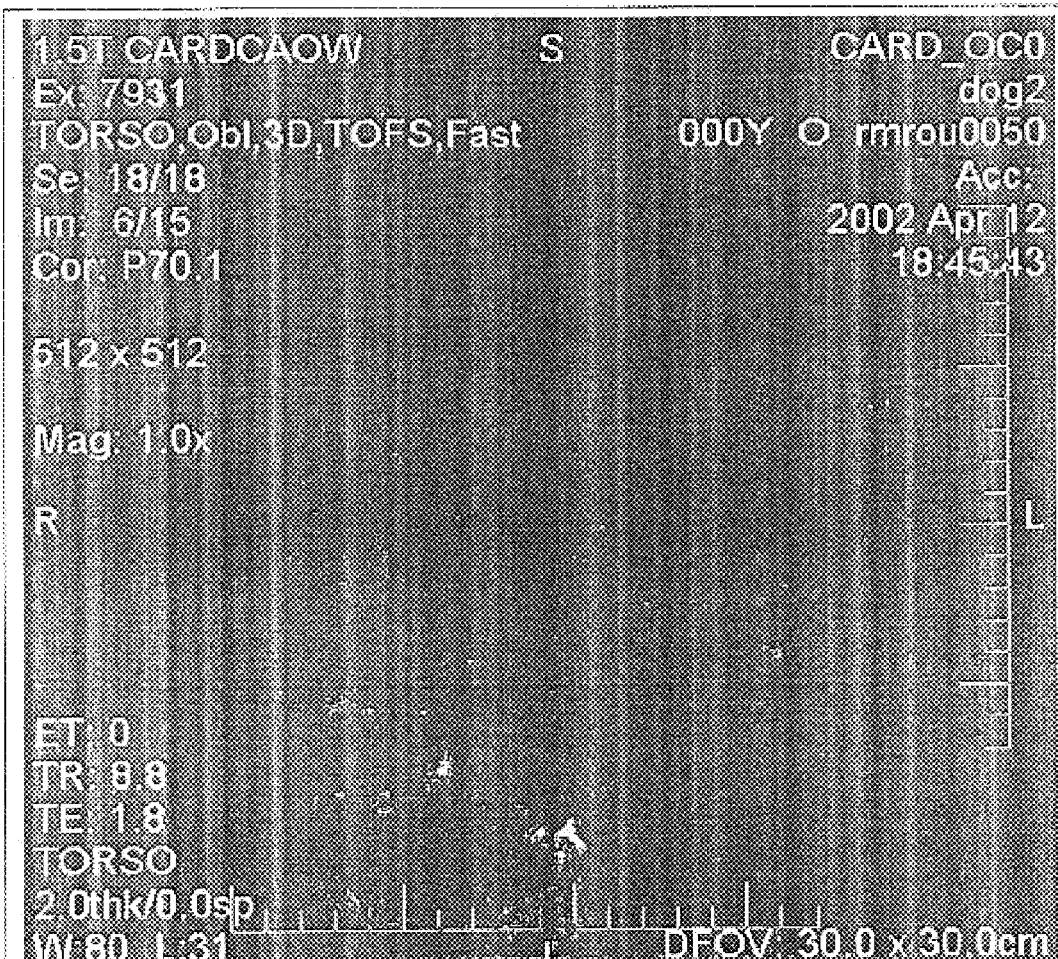
FIG. 15 is a temporal MR snapshot of a DTPA[Gd(III)] attached and then gelatin encapsulated PE rod in a canine aorta. More particularly.

The DTPA[Gd(III)] attached and then cross-linked gelatin encapsulated PE rods (length 40 cm, diameter 2 mm) were imaged in canine aorta, the results of which are shown in FIG. 15. More particularly, FIG. 15 is a 3D maximum-intensity-projection (MIP) MR image of the PE rods 25 minutes after it was inserted into the canine aorta. The coated PE rods is clearly visible as shown in FIG. 15, and the signal intensity improved with time.

Example 12
Coupling of Diethylenetriaminepentaacetic Acid (DTPA) to Poly(N-[3-aminopropyl] methylacrylamide); Functional Coating on a Guide-wire; Cross-linking of the Gel-coating on the Guide-wire; and Complexing Gd(III) to the DPTA-linked Poly(N-[3-aminopropyl] methylacrylamide) and DTPA Dispersed in the Gel-coating. The Schematic Structure of the Coating and Chemistry Detail are Illustrated in FIGS. 16 and 17.

Again, the same materials as set forth in Example 11 were used in conjunction with Example 12. The guide wire used in this example is a commercial product from Medi-tech, Inc (480 Pleasant street/P.O. Box 7407, Watertown, Mass. 02272) with the diameter of 0.038 in. and length of 150 cm.

Coupling of Diethylenetriaminepentaacetic acid (DTPA) to poly(N-[3-aminopropyl] methylacrylamide)

0.79 g of DTPA (2 mmol) was dissolved in 20 mL DMSO at 80° C. for 30 minutes, and then the solution was cooled to room temperature. 0.14 g poly(N-[3-aminopropyl] methylacrylamide) having one mmol of repeating unit and separately synthesized in-house was dissolved with 0.206 g DCC (1 mmol) 20 mL of DMSO. The solution was slowly added to the DTPA solution dropwise with stirring. When all of the polymer and DCC solution was added, the final mixture was stirred for 8 hours at room temperature and then filtered. 200 mL of diethyl ether was added to the filtered solution to precipitate the product, a mixture of free DTPA and DTPA linked polymer. The solid product was collected by filtration and dried.

Functional Coating on a Guide-wire 0.5 g of the above product and 20 g gelatin were dissolved in 100 mL of distilled water at 60° C. for 1 hour with stirring. The solution was transferred to a long glass tube with a jacket and kept in the water bath in the jacket at 35° C. Part of (60 cm) a guide-wire was then dipped into the solution. After removing the guide-wire from the solution, it was cooled to room temperature in order to allow a gel-coating to chill-set, i.e., to form as a hydrogel coating on the wire surface. The final dry thickness of gel-coating was around 30 $\mu$m. The same procedure may be repeated to overcoat additional layers of the gel. When it was repeated twice, the final dry thickness of gel-coating was around 60 $\mu$m.

Cross-linking of the Gel-coating on a Guide-wire

Several minutes after the gel-coating, the coated guide wire was soaked in 0.5% glutaraldehyde 300 ml for 2 hours to cross-link the gelatin and the primary polymer. Then, the rods were first washed with distilled water and soaked further in distilled water for 2 hours to remove all soluble and diffusible materials such as free DTPA and glutaraldehyde.

Complexing of Gd(III) to the DPTA-linked Poly(N-[3-aminopropyl] methylacrylamide) and DTPA Dispersed in the Gel-coating After the cross-linking the gel-coating on the guide-wire with glutaraldehyde, the wire was soaked in a solution of 1.70 g $GdCl_3.6H_2O$ dissolved in 300 mL of distilled water for 8 to 10 hours. Then, the wire was washed with distilled water and further soaked for 8 to 10 hours to remove free $GdCl_3$. Finally the gel-coated wire was dried in air.

Results

The guide-wire with a functional gelatin coating, in which DTPA[Gd(III)] linked polymer was dispersed and cross-linked with gelatin, was imaged in a canine aorta using 2D and 3D RF spoiled gradient-recalled echo (SPGR) sequences. Typical scan parameters for 2D SPGR sequence were: TR=18 ms, TE=3.7 ms. acquisition matrix=256×256, FOV=20 cm×20 cm, slice thickness=3 mm, and flip angle=30°. Typical scan parameters for 3D SPGR sequence were: TR=8.8 ms, TE=1.8 ms. acquisition matrix=512×192, FOV=20 cm×20 cm, slice thickness=2 mm, and flip angle=60°.

Figure 18:
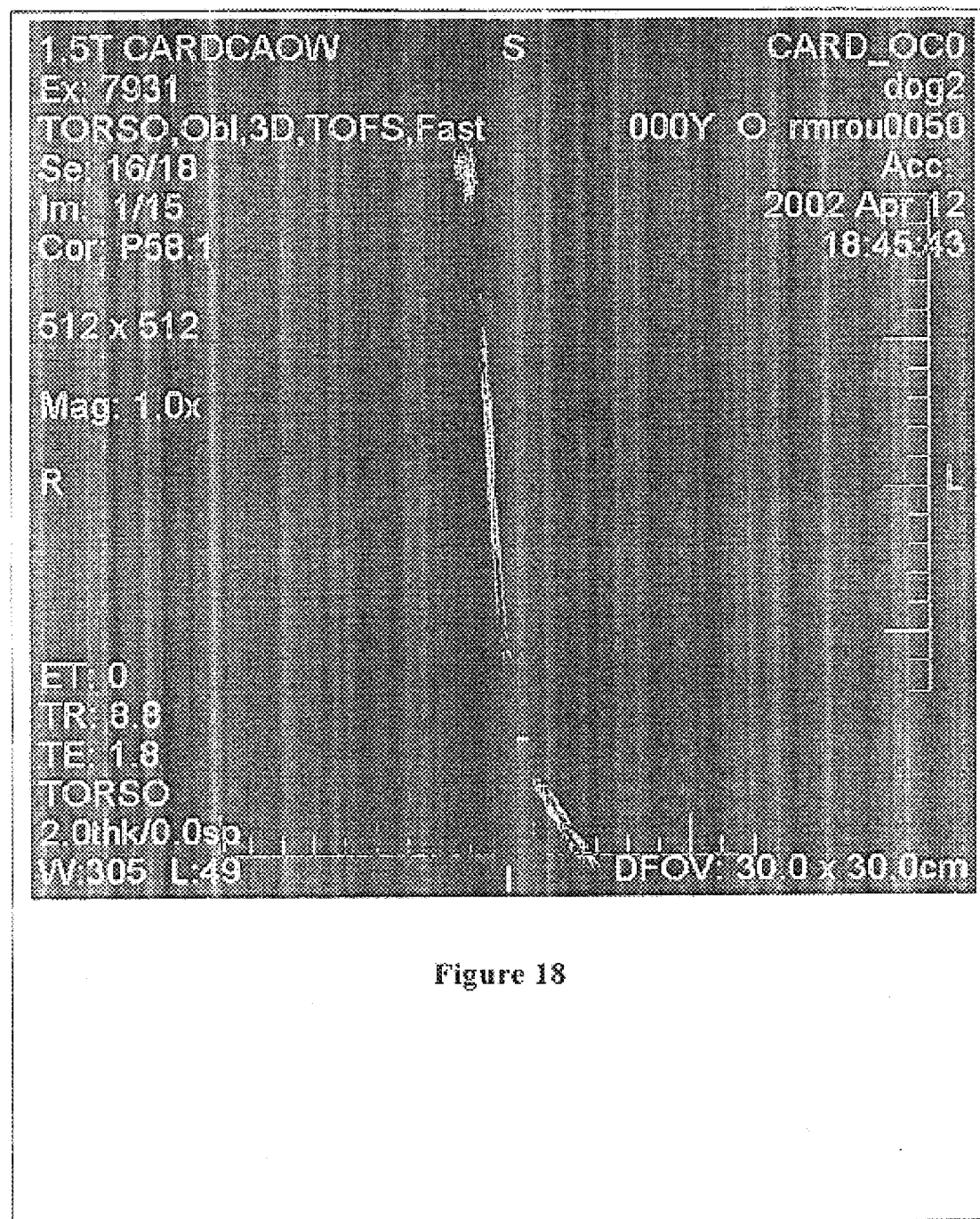
FIG. 18 is a temporal MR snapshot of a guide-wire with a functional gelatin coating in which a DTPA[Gd(III)] linked polymer was dispersed and cross-linked with gelatin. More particularly.

These results are shown in FIG. 18. In the experiments, the thickness of the gelatin coating is about 60 $\mu$m. The diameter of the coated guide wire is about 0.038 in and the length of coated part is around 60 cm. FIG. 18 is the 3D maximum-intensity-projection (MIP) MR image of the guide wire 10 minutes after it was inserted into the canine aorta. The coated guide wire is visible in canine aorta as shown in FIG. 18. The signal of the coated guide-wire is very bright and improved with time.

Example 13

Synthesizing Diethylenetriaminepentaacetic Dianhydride (DTPAda); Functional Coating on a Guide Wire and Catheter; Cross-linking of the Gel-coating on the Guide Wire and Catheter; and Complexing Gd(III) to the DPTA-linked Gelatin Dispersed in the Gel-coating. The Schematic Structure of the Coating and Chemistry Detail are Illustrated in FIG. 19 and 20

Again, the same materials set forth in Example 11–12 were used in conjunction with Example 13. The catheter used in this example is a commercial product from Target Therapeutics, Inc. (San Jose, Calif. 95134) having a length of 120 cm and diameter of 4.0F.

Synthesizing Diethylenetriaminepentaacetic Dianhydride (DTPAda)

1.08 gram of DTPA (2.7 mmol), 2 mL acetic anhydride and 1.3 mL pyridine were stirred for 48 hours at 60° C. and then the reaction mixture was filtered at room temperature. The solid product was washed to be free of pyridine with acetic anhydride and then with diethyl ether and is dried.

Coupling of Diethylenetriaminepentaacetic acid (DTPA) to Gelatin 0.6 g gelatin (0.16 mmol of lysine residue) was dissolved in 20 mL of distilled water at 60° C. for 1 hours. Then the solution was kept above 40° C. 1/3 of the gelatin solution and 1/3 of the total DTPAda weighing 0.5 g (1.4 mmol) were successively added to 20 mL of water at 35° C. with stirring. This step was carried out by keeping the solution pH constant at 10 with 6 N NaOH. This operation was repeated until all the reagents were consumed. The final mixture was stirred for an additional 4 hours. Then, the pH of the mixture was adjusted to 6.5 by adding 1 N $HNO_3$.

Functional Coating on Guide—Wire and Catheter 5.0 g DTPA linked gelatin and DTPA mixture (around 1:1 by weight) and 20 g of fresh gelatin were dissolved in 100 mL distilled water at 60° C. for one hour with stirring. The solution was transferred to a long glass tube with a jacket and kept in the water bath in the jacket at 35° C. A part of (60 cm) a guide wire was then dipped into the solution. After removing the guide-wire from the solution, it was cooled to room temperature in order to allow a gel-coating to chill-set, i.e., to form as a hydrogel coating on the rod surface. The final dry thickness of gel-coating was around 30 $\mu$m. The same procedure may be repeated to overcoat additional layers of the gel. When it was repeated twice, the final dry thickness of gel-coating was around 60 $\mu$m.

Using the same procedure, a part of (45 cm) catheter (diameter 4.0F) was coated with such functional gelatin, in which DTPA linked gelatin dispersed.

Cross-linking of the Gel-coating on PE Rods

Several minutes after the gel-coating, the coated guide wire and catheter were soaked in 0.5% glutaraldehyde 300 ml for 2 hours in order to cross-link the gelatin coating. Then, guide wire and catheter were first washed with distilled water and soaked further for 2 hours to remove all soluble and diffusible materials such as free DTPA and glutaraldehyde.

Complexing Gd(III) to the DPTA-linked Gelatin Dispersed in the Gel-coating

After the cross-linking the gel-coating on guide wire and catheter with glutaraldehyde, the rods were soaked in a solution of 1.7 g $GdCl_3.6H_2O$ dissolved in 300 ml of distilled water for 8 to 10 hours. Then the guide-wire and catheter were washed with distilled water and further soaked for 8 to 10 hours to remove the free $GdCl_3$. Finally the gel-coated guide-wire and catheter were dried in air.

Results

Figure 21:
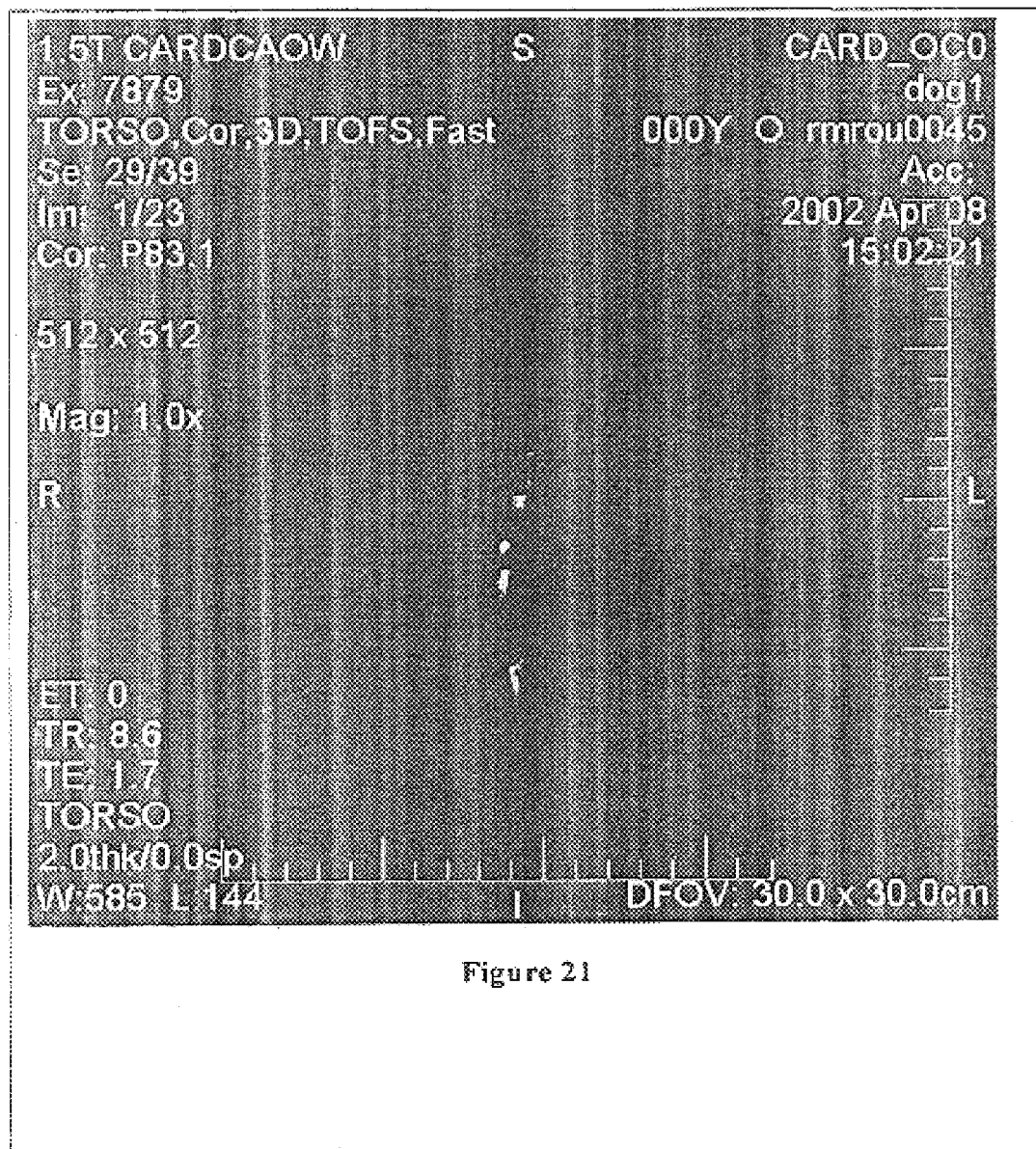
FIG. 21 is a temporal MR snapshot of a guide-wire with a functional gelatin coating in which a DTPA[Gd(III)] linked gelatin was dispersed and cross-linked. More particularly.

The guide-wire and catheter with a functional gelatin coating, in which DTPA[Gd(III)] linked gelatin was dispersed, was imaged in a canine aorta using 2D and 3D RF spoiled gradient-recalled echo (SPGR) sequences. Typical scan parameters for 2D SPGR sequence were: TR=18 ms, TE=3.7 ms. acquisition matrix=256×256, FOV=20 cm×20 cm, slice thickness=3 mm, and flip angle=30°. Typical scan parameters for 3D SPGR sequence were: TR=8.8 ms, TE=1.8 ms. acquisition matrix=512×192, FOV=20 cm×20 cm, slice thickness=2 mm, and flip angle=60°. These results are shown in FIG. 20. In the experiments, the thickness of gelatin coating is 60 μm. The diameter of the coated guide-wire is 0.038in and the length of coated part is around 60 cm. FIG. 21 is the 3D MIP MR image of the guide wire 30 minutes after it was inserted into the canine aorta. The coated guide-wire is visible in canine aorta as shown in FIG. 21. The signal of the coated guide-wire improved with time.

Figure 22:
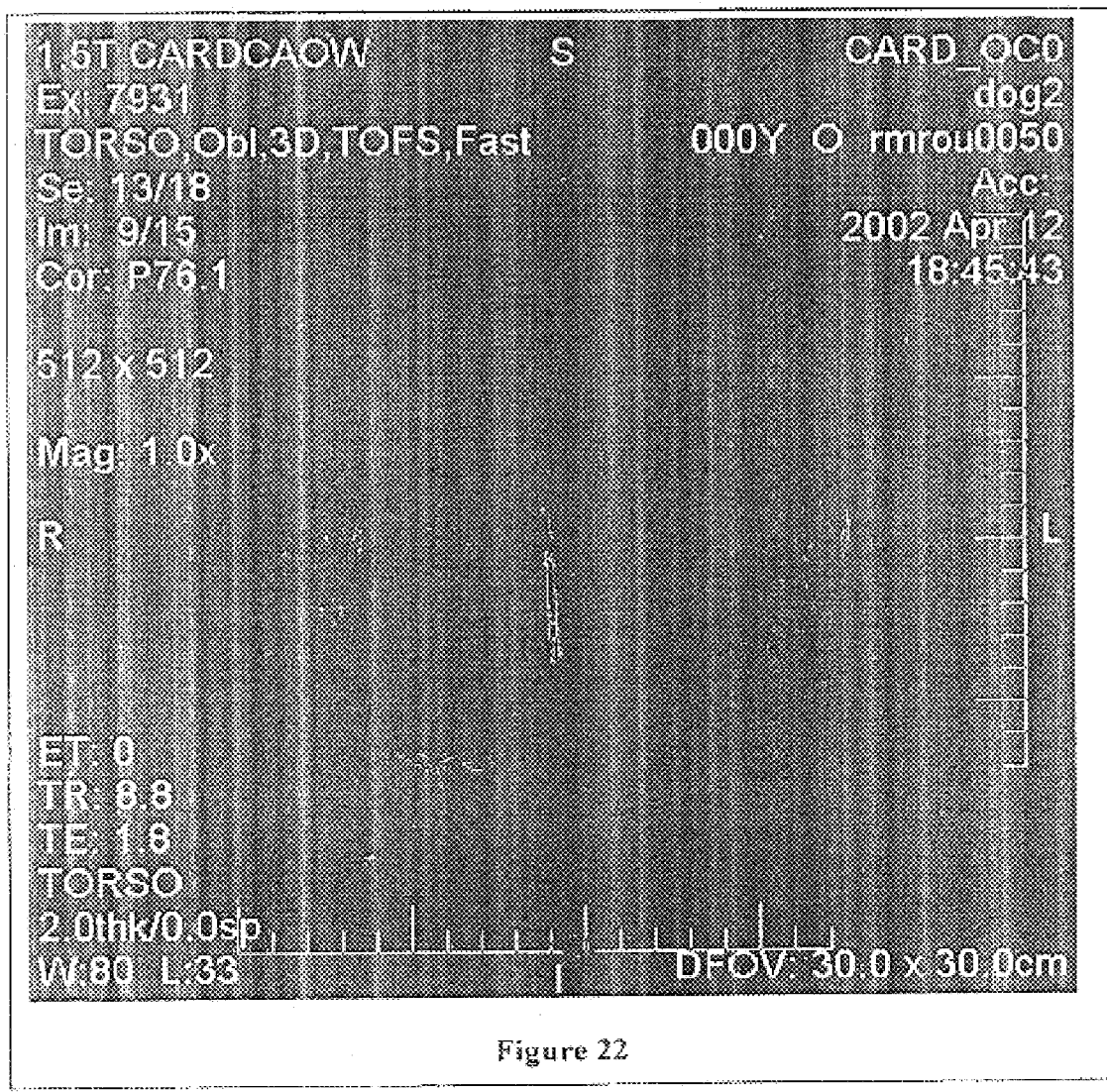
FIG. 22 is a temporal MR snapshot of a catheter with a functional gelatin coating in which a DTPA[Gd(III)] linked gelatin was dispersed and cross-linked. More particularly.

The catheter with a functional gelatin coating, in which DTPA[Gd(III)] linked gelatin was dispersed, was imaged in canine aorta, the results of which are shown in FIG. 22. In the experiments, the thickness of gelatin coating is 30 μm. The diameter of the coated catheter is 4.0F and the length of coated part is around 45 cm. Typical scan parameters for 3D SPGR sequence were: TR=8.8 ms, TE=1.8 ms. acquisition matrix=512×192, FOV=20 cm×20 cm, slice thickness 2 mm, and flip angle=60°. FIG. 22 is the 3D MIP MR image of the catheter 20 minutes after it was inserted into the canine aorta. The coated catheter is visible and bright in canine aorta as shown in FIG. 22. The MR signal intensity of coated catheter improved with time.

In summary, the present invention provides a method of visualizing pre-existing medical devices under MR guidance utilizing a coating, which is a polymeric-paramagnetic ion complex, on the medical devices. The methods practiced in accordance with the present invention provide various protocol for applying and synthesizing a variety of coatings.

While the present invention has now been described and exemplified with some specificity, those skilled in the art will appreciate the various modifications, including variations, additions, and omissions, which may be made in what has been described. Accordingly, it is intended that these modifications also be encompassed by the present invention and that the scope of the present invention be limited solely by the broadest interpretation that can lawfully be accorded the appended claims. All printed publications, patents and patent applications referred to herein are hereby fully incorporated by reference.

We claim:

1. A method of making a medical device magnetic-resonance imageable, the method comprising:
providing a coating on the medical device in which a paramagnetic-metal ion/chelate complex is encapsulated by a first hydrogel, a chelate of the paramagnetic-metal-ion/chelate complex being linked to a functional group, and the functional group being an amine group or a carboxyl group.

2. The method of claim 1, wherein at least a portion of the medical device is made from a solid-base polymer, and the method further comprises treating the solid-base polymer to yield the functional group thereon, the complex accordingly being covalently linked to the medical device.

3. The method of claim 2, wherein treating the solid-base polymer comprises plasma treating the solid-base polymer with a plasma gas which is hydrazine, ammonia, a chemical moiety of a nitrogen-hydrogen combination or combinations thereof, and wherein the resulting plasma-treated functional group is an amine group.

4. The method of claim 2, wherein treating the solid-base polymer comprises plasma treating the solid-base polymer with a plasma gas which is carbon dioxide or oxygen, and wherein the resulting plasma treated functional group is a carboxyl group.

5. The method of claim 2, wherein treating the solid-base polymer comprises melt coating with a hydrophilic polymer or precoating with a hydrophilic polymer containing primary amine groups.

6. The method of claim 2, wherein the chelate is covalently linked to the functional group by an amide linkage.

7. The method of claim 2, wherein the polymer is selected from the group consisting of polyethylenes, polypropylenes, polyesters, polyamides, polytetrafluoroethylene, polyurethanes, polyamino undecanoic acid, polydimethylsiloxane, polyglycols, polyoxyethylenes, polysorbate 60, stearate and palmitate esters of sorbitol copolymerized with ethylene glycol, polyvinyl acetate phthalate, polyvinyl alcohol and polystyrene sulfonate.

8. The method of claim 2, wherein the paramagnetic-metal ion is designated as $M^{n+}$, and M is a lanthanide or a transition metal which is iron, manganese, chromium, cobalt or nickel, and n is an integer that is 2 or greater.

9. The method of claim 8, wherein M is a lanthanide and the lanthanide is gadolinium.

10. The method of claim 2, wherein the chelate is selected from the group consisting of diethylenetriaminepentaacetic acid (DTPA), 1,4,7,10-tetracyclododecane-N,N',N'',N'''-tetraacetic acid (DOTA) and 1,4,8,11-tetraazacyclotradecane-N,N',N'',N'''-tetraacetic acid (TETA), diethylenetriaminepentaacetic acid-N,N'-bis (methylamide) (DTPA-BMA), diethylenetriaminepentaacetic acid-N,N'-bis(methoxyethylamide) (DTPA-BMEA), s-4-(4-ethoxybenzyl)-3,6,9-tris[(carboxylatomethyl)]-3,6,9-triazaundecanedionic acid (EOB-DTPA), benzyloxypropionictetraacetate(BOPTA), (4R)-4-[bis (carboxymethylamino]-3,6,9-triazaundecanedionic acid (MS-325), 1,4,7-tris(carboxymethyl)-10-(2'-hydroxypropyl)-1,4,7,10-tetraazacyclododecane (HP-DO3A), and DO3A-butrol.

11. The method of claim 10, wherein the chelate is DTPA.

12. The method of claim 2, wherein the first hydrogel is collagen, gelatin, hyaluronate, fibrin, alginate, agarose, chitosan, poly(acrylic acid), poly(acrylamide), poly(2-hydroxyethyl methacrylate), poly(N-isopropylacrylamide), poly(ethylene glycol)/poly(ethylene oxide), poly(ethylene oxide)-block-poly(lactic acid), poly(vinyl alcohol), polyphosphazenes, polypeptides or a combination thereof.

13. The method of claim 2, wherein a linker or spacer molecule links the chelate of the paramagnetic-metal-ion/chelate complex to the functional group, and the linker or spacer molecule is lactam or diamine.

14. The method of claim 2, further comprising chill-setting the coating after the coating is provided on the medical device.

15. The method of claim 2, further comprising using a cross-linker to cross-link the polymer and the first hydrogel to form a hydrogel overcoat.

16. The method of claim 15, wherein the polymer contains an amine group and the hydrogel contains an amine group.

17. The method of claim 15, wherein the cross-linker is glutaraldehyde.

18. The method of claim 17, wherein the polymer has an amine group, and the cross-linker connects the amine group to an aldehyde moiety of the glutaraldehyde.

19. The method of claim 1, wherein the functional group is a functional group of a polymer.

20. The method of claim 19, further comprising chill-setting the coating after providing the coating on the medical device.

21. The method of claim 19, further comprising using a cross-linker to cross-link the polymer and the first hydrogel to form a hydrogel overcoat.

22. The method of claim 19, wherein the polymer is not covalently linked to the medical device.

23. The method of claim 19, wherein the paramagnetic-metal ion is designated as $M^{n+}$, and M is a lanthanide or a transition metal which is iron, manganese, chromium, cobalt or nickel, and n is an integer that is 2 or greater.

24. The method of claim 23, wherein M is a lanthanide and the lanthanide is gadolinium.

25. The method of claim 19, wherein the chelate is selected from the group consisting of diethylenetriaminepentaacetic acid (DTPA), 1,4,7,10-tetracyclododecane-N,N',N'',N'''-tetraacetic acid (DOTA) and 1,4,8,11-tetraazacyclotradecane-N,N',N'',N'''-tetraacetic acid (TETA). diethylenetriaminepentaacetic acid-N,N'-bis(methylamide) (DTPA-BMA), diethylenetriaminepentaacetic acid-N,N'-bis(methoxyethylamide) (DTPA-BMEA), s-4-(4-ethoxybenzyl)-3,6,9-tris[(carboxylatomethyl)]-3,6,9-triazaundecanedionic acid (EOB-DTPA), benzyloxypropionictetraacetate(BOPTA), (4R)-4-[bis(carboxymethylamino]-3,6,9-triazaundecanedionic acid (MS-325), , 1,4,7-tris(carboxymethyl)-10-(2'-hydroxypropyl)-1,4,7,10-tetraazacyclododecane (HP-DO3A), and DO3A-butrol.

26. The method of claim 19, wherein the first hydrogel is collagen, gelatin, hyaluronate, fibrin, alginate, agarose, chitosan, poly(acrylic acid), poly(acrylamide), poly(2-hydroxyethyl methacrylate), poly(N-isopropylacrylamide), poly(ethylene glycol)/poly(ethylene oxide), poly(ethylene oxide)-block-poly(lactic acid), poly(vinyl alcohol), polyphosphazenes, polypeptides or a combination thereof.

27. The method of claim 19, wherein a linker or spacer molecule links the chelate of the paramagnetic-metal-ion/chelate complex to the functional group, and the linker or spacer molecule is lactam or diamine.

28. The method of claim 1, wherein the functional group is a functional group of a second hydrogel.

29. The method of claim 28, wherein the first hydrogel and the second hydrogel are selected from the group consisting of collagen, gelatin, hyaluronate, fibrin, alginate, agarose, chitosan, poly(acrylic acid), poly(acrylamide), poly(2-hydroxyethyl methacrylate), poly(N-isopropylacrylamide), poly(ethylene glycol)/poly(ethylene oxide), poly(ethylene oxide)-block-poly(lactic acid), poly(vinyl alcohol), a polyphosphazene, a polypeptide and combinations thereof, and wherein the first hydrogel and the second hydrogel are the same or different.

30. The method of claim 29, wherein the first hydrogel and second hydrogel are gelatin.

31. The method of claim 28, wherein the complex is mixed with the first hydrogel to produce the coating.

32. The method of claim 28, further comprising chill-setting the coating after providing the coating thereon.

33. The method of claim 28, further comprising using a cross-linker to cross-link the first hydrogel and the second hydrogel to form a hydrogel overcoat.

34. The method of claim 33, wherein the cross-linker is glutaraldehyde.

35. The method of claim 28, wherein the paramagnetic-metal ion is designated as $M^{n+}$, and M is a lanthanide or a transition metal which is iron, manganese, chromium, cobalt or nickel, and n is an integer that is 2 or greater.

36. The method of claim 35, wherein M is a lanthanide and the lanthanide is gadolinium.

37. The method of claim 28, wherein the chelate is selected from the group consisting of diethylenetriaminepentaacetic acid (DTPA), 1,4,7,10-tetracyclododecane-N,N',N'',N'''-tetraacetic acid (DOTA) and 1,4,8,11-tetraazacyclotradecane-N,N',N'',N'''-tetraacetic acid (TETA). diethylenetriaminepentaacetic acid-N,N'-bis(methylamide) (DTPA-BMA), diethylenetriaminepentaacetic acid-N,N'-bis(methoxyethylamide) (DTPA-BMEA), s-4-(4-ethoxybenzyl)-3,6,9-tris[(carboxylatomethyl)]-3,6,9-triazaundecanedionic acid (EOB-DTPA), benzyloxypropionictetraacetate(BOPTA), (4R)-4-[bis(carboxymethylamino]-3,6,9-triazaundecanedionic acid (MS-325), 1,4,7-tris(carboxymethyl)-10-(2'-hydroxypropyl)-1,4,7,10-tetraazacyclododecane (HP-DO3A), and DO3A-butrol.

38. The method of claim 35, wherein the first hydrogel is gelatin, the second hydrogel is gelatin and the chelate is DTPA.

39. The method of claim 28, wherein a linker or spacer molecule links the chelate of the paramagnetic-metal-ion/chelate complex to the functional group, and the linker or spacer molecule is lactam or diamine.

40. A medical device capable of being magnetic-resonance imaged, the device comprising:
    a chelate linked to a functional group, the functional group being an amino or a carboxyl group;
    a paramagnetic-metal ion coordinated with the chelate to form a paramagnetic-metal-ion/chelate complex; and
    a first hydrogel encapsulating the paramagnetic-metal-ion/chelate complex.

41. The device of claim 40, wherein at least a portion of the medical device is made of a solid-base polymer, and the functional group is a functional group on the solid-base polymer, and the paramagnetic-metal-ion/chelate complex is accordingly covalently linked to the medical device.

42. The device of claim 41, wherein the functional group on the solid-base polymer is formed by treating the substrate to yield the functional group thereon.

43. The device of claim 42, wherein treating the solid-base polymer comprises plasma treating the solid-base polymer with a plasma gas which is carbon dioxide, oxygen, hydrazine, ammonia, a chemical moiety of a nitrogen-hydrogen combination or combinations thereof.

44. The device of claim 41, wherein the polymer is selected from the group consisting of polyethylenes, polypropylenes, polyesters, polyamides, polytetrafluoroethylene, polyurethanes, polyamino undecanoic acid, polydimethylsiloxane, polyglycols, polyoxyethylenes, polysorbate 60, stearate and palmitate esters of sorbitol copolymerized with ethylene glycol, polyvinyl acetate phthalate, polyvinyl alcohol and polystyrene sulfonate.

45. The device of claim 41, wherein the paramagnetic-metal ion is designated as $M^{n+}$, and M is a lanthanide or a transition metal which is iron, manganese, chromium, cobalt or nickel, and n is an integer that is 2 or greater.

46. The device of claim 45, wherein M is a lanthanide and the lanthanide is gadolinium.

47. The device of claim 41, wherein the chelate is selected from the group consisting of diethylenetriaminepentaacetic acid (DTPA), 1,4,7,10-tetracyclododecane-N,N',N'',N'''-tetraacetic acid (DOTA) and 1,4,8,11-tetraazacyclotradecane-N,N',N'',N'''-tetraacetic acid (TETA) ., diethylenetriaminepentaacetic acid-N,N'-bis(methylamide) (DTPA-BMA), diethylenetriaminepentaacetic acid-N,N'-bis(methoxyethylamide) (DTPA-BMEA), s-4-(4-ethoxybenzyl)-3,6,9-tris[(carboxylatomethyl)]-3,6,9-triazaundecanedionic acid (EOB-DTPA), benzyloxypropionictetraacetate(BOPTA), (4R)-4-[bis(carboxymethylamino]-3,6,9-triazaundecanedionic acid (MS-325), 1,4,7-tris(carboxymethyl)-10-(2'-hydroxypropyl)-1,4,7,10-tetraazacyclododecane (HP-DO3A), and DO3A-butrol.

48. The device of claim 41, wherein the first hydrogel is collagen, gelatin, hyaluronate, fibrin, alginate, agarose, chitosan, poly(acrylic acid), poly(acrylamide), poly(2-hydroxyethyl methacrylate), poly(N-isopropylacrylamide), poly(ethylene glycol)/poly(ethylene oxide), poly(ethylene oxide)-block-poly(lactic acid), poly(vinyl alcohol), polyphosphazenes, polypeptides or a combination thereof.

49. The device of claim 41, wherein a linker or spacer molecule links the chelate of the paramagnetic-metal-ion/chelate complex to the functional group, and the linker or spacer molecule is lactam or diamine.

50. The device of claim 41, wherein the polymer and the first hydrogel are cross-linked to produce a hydrogel overcoat using a cross-linker.

51. The device of claim 50, wherein the cross-linker is glutaraldehyde.

52. The device of claim 40, wherein the functional group is a functional group of a polymer.

53. The device of claim 52, wherein the polymer is not covalently linked to the medical device.

54. The device of claim 52, wherein a cross-linker cross-links the polymer and the first hydrogel to produce a hydrogel overcoat.

55. The device of claim 54, wherein the cross-linker is glutaraldehyde.

56. The device of claim 52, wherein the paramagnetic-metal ion is designated as $M^{n+}$, and M is a lanthanide or a transition metal which is iron, manganese, chromium, cobalt or nickel, and n is an integer that is 2 or greater.

57. The device of claim 56, wherein M is a lanthanide and the lanthanide is gadolinium.

58. The device of claim 52, wherein the chelate is selected from the group consisting of diethylenetriaminepentaacetic acid (DTPA), 1,4,7,10-tetracyclododecane-N,N',N'',N'''-tetraacetic acid (DOTA) and 1,4,8,11-tetraazacyclotradecane-N,N',N'',N'''-tetraacetic acid (TETA)., diethylenetriaminepentaacetic acid-N,N'-bis (methylamide) (DTPA-BMA), diethylenetriaminepentaacetic acid-N,N'-bis (methoxyethylamide) (DTPA-BMEA), s-4-(4-ethoxybenzyl)-3,6,9-tris[(carboxylatomethyl)]-3,6,9-triazaundecanedionic acid (EOB-DTPA), benzyloxypropionictetraacetate(BOPTA), (4R)-4-[bis(carboxymethylamino]-3,6,9-triazaundecanedionic acid (MS-325), 1,4,7-tris(carboxymethyl)-10-(2'-hydroxypropyl)-1,4,7,10-tetraazacyclododecane (HP-DO3A), and DO3A-butrol.

59. The device of claim 58, wherein the chelate is a DTPA.

60. The device of claim 52, wherein the first hydrogel is collagen, gelatin, hyaluronate, fibrin, alginate, agarose, chitosan, poly(acrylic acid), poly(acrylamide), poly(2-hydroxyethyl methacrylate), poly(N-isopropylacrylamide), poly(ethylene glycol)/poly(ethylene oxide), poly(ethylene oxide)-block-poly(lactic acid), poly(vinyl alcohol), polyphosphazenes, polypeptides or a combination thereof.

61. The device of claim 52, wherein a linker or spacer molecule links the paramagnetic-metal-ion/chelate complex to the functional group, and the linker or spacer molecule is lactam or diamine.

62. The device of claim 40, wherein the functional group is a functional group of a second hydrogel.

63. The device of claim 62, wherein the first hydrogel and the second hydrogel are selected from the group consisting of collagen, gelatin, hyaluronate, fibrin, alginate, agarose, chitosan, poly(acrylic acid), poly(acrylamide), poly(2-hydroxyethyl methacrylate), poly(N-isopropylacrylamide), poly(ethylene glycol)/poly(ethylene oxide), poly(ethylene oxide)-block-poly(lactic acid), poly(vinyl alcohol), a polyphosphazene, a polypeptide and combinations thereof, and wherein the first hydrogel and the second hydrogel are the same or different.

64. The device of claim 62, wherein the first hydrogel and second hydrogel are gelatin.

65. The device of claim 62, wherein the first hydrogel and the second hydrogel are cross-linked using a cross-linker to form a hydrogel overcoat.

66. The device of claim 65, wherein the cross-linker is glutaraldehyde.

67. The device of claim 62, wherein the paramagnetic-metal ion is designated as $M^{n+}$, and M is a lanthanide or a transition metal which is iron, manganese, chromium, cobalt or nickel, and n is an integer that is 2 or greater.

68. The device of claim 67, wherein M is a lanthanide and the lanthanide is gadolinium.

69. The device of claim 62, wherein the chelate is selected from the group consisting of diethylenetriaminepentaacetic acid (DTPA), 1,4,7,10-tetracyclododecane-N,N',N'',N'''-tetraacetic acid (DOTA) and 1,4,8,11-tetraazacyclotradecane-N,N',N'',N'''-tetraacetic acid (TETA)., diethylenetriaminepentaacetic acid-N,N'-bis (methylamide) (DTPA-BMA), diethylenetriaminepentaacetic acid-N,N'-bis (methoxyethylamide) (DTPA-BMEA), s-4-(4-ethoxybenzyl)-3,6,9-tris[(carboxylatomethyl)]-3,6,9-triazaundecanedionic acid (EOB-DTPA), benzyloxypropionictetraacetate(BOPTA), (4R)-4-[bis(carboxymethylamino]-3,6,9-triazaundecanedionic acid (MS-325), , 1,4,7-tris(carboxymethyl)-10-(2'-hydroxypropyl)-1,4,7,10-tetraazacyclododecane (HP-DO3A), and DO3A-butrol.

70. The device of claim 62, wherein a linker or spacer molecule links the paramagnetic-metal-ion/chelate complex to the functional group, and the linker or spacer molecule is lactam or diamine.

71. A method of reducing the mobility of paramagnetic-metal-ion/chelate complexes covalently linked to a solid-base polymer of a medical device, the method comprising:
providing a medical device having paramagnetic-metal-ion/chelate complexes covalently linked to the solid-base polymer of the medical device; and
encapsulating at least one of the paramagnetic-metal-ion/chelate complexes covalently linked to the medical device with a hydrogel, the hydrogel reducing the mobility of at least one of the paramagnetic-metal-ion/chelate complexes, and thereby enhancing the magnetic-resonance imageability of the medical device.

72. The method of claim 71, wherein providing a medical device having paramagnetic-metal-ion/chelate complexes covalently linked to the solid-base polymer of the medical device further comprises plasma treating at least a portion of the solid-base polymer of the medical device before covalently linking the complex thereto, in order to provide functional groups selected from the group consisting of amino groups and carboxyl groups linked thereto.

73. The method of claim 72, wherein providing a medical device having paramagnetic-metal-ion/chelate complexes covalently linked to the solid-base polymer of the medical device further comprises covalently linking the paramagnetic-metal-ion/chelate complexes to the functional groups.

74. The method of claim 73, wherein a linker or a spacer molecule links the paramagnetic-metal-ion/chelate complexes to the functional groups, and the linker or spacer molecule is lactam or diamine.

75. The method of claim 71, wherein the hydrogel is collagen, gelatin, hyaluronate, fibrin, alginate, agarose, chitosan, poly(acrylic acid), poly(acrylamide), poly(2-hydroxyethyl methacrylate), poly(N-isopropylacrylamide), poly(ethylene glycol)/poly(ethylene oxide), poly(ethylene oxide)-block-poly(lactic acid), poly(vinyl alcohol), polyphosphazenes, polypeptides or a combination thereof.

76. The method of claim 71, wherein the polymer is selected from the group consisting of polyethylenes, polypropylenes, polyesters, polyamides, polytetrafluoroethylene, polyurethanes, polyamino undecanoic acid, polydimethylsiloxane, polyglycols, polyoxyethylenes, polysorbate 60, stearate and palmitate esters of sorbitol copolymerized with ethylene glycol, polyvinyl acetate phthalate, polyvinyl alcohol and polystyrene sulfonate.

77. The method of claim 71, wherein the paramagnetic-metal ion is designated as $M^{n+}$, and M is a lanthanide or a transition metal which is iron, manganese, chromium, cobalt or nickel, and N is an integer that is 2 or greater.

78. The method of claim 77, wherein M is a lanthanide and the lanthanide is gadolinium.

79. The method of claim 71, wherein the chelate is selected from the group consisting of diethylenetriaminepentaacetic acid (DTPA), 1,4,7,10-tetracyclododecane-N,N',N",N'"-tetraacetic acid (DOTA) and 1,4,8,11-tetraazacyclotradecane-N,N',N",N'"-tetraacetic acid (TETA)., diethylenetriaminepentaacetic acid-N,N'-bis(methylamide) (DTPA-BMA), diethylenetriaminepentaacetic acid-N,N'-bis(methoxyethylamide) (DTPA-BMEA), s-4-(4-ethoxybenzyl)-3,6,9-tris[(carboxylatomethyl)]-3,6,9-triazaundecanedionic acid (EOB-DTPA), benzyloxypropionictetraacetate(BOPTA), (4R)-4-[bis(carboxymethylamino]-3,6,9-triazaundecanedionic acid (MS-325), 1,4,7-tris(carboxymethyl)-10-(2'-hydroxypropyl)-1,4,7,10-tetraazacyclododecane (HP-DO3A), and DO3A-butrol.

80. A method manufacturing a magnetic-resonance-imageable medical device, the method comprising:
providing a medical device; and
cross-linking a chain with a first hydrogel to form a hydrogel overcoat on at least a portion of the medical device, the chain having a paramagnetic-metal-ion/chelate complex linked thereto.

81. The method of claim 80, wherein the complex is linked to the chain by a functional group on the chain, the functional group being an amine group or a carboxyl group.

82. The method of claim 81, wherein the paramagnetic-metal-ion/chelate complex is formed by coordinating a paramagnetic-metal-ion with the chelate.

83. The method of claim 80, wherein the chain is a polymer chain.

84. The method of claim 83, wherein the medical device has a surface, and the surface is at least partially made from or coated with a solid-base polymer including the polymer chain, and the complex is thereby covalently linked to the medical device.

85. The method of claim 84, wherein the functional group is formed by plasma treating the solid-base polymer.

86. The method of claim 84, wherein the solid-base polymer is selected from the group consisting of polyethylenes, polypropylenes, polyesters, polyamides, polytetrafluoroethylene, polyurethanes, polyamino undecanoic acid, polydimethylsiloxane, polyglycols, polyoxyethylenes, polysorbate 60, stearate and palmitate esters of sorbitol copolymerized with ethylene glycol, polyvinyl acetate phthalate, polyvinyl alcohol and polystyrene sulfonate.

87. The method of claim 84, wherein the paramagnetic-metal ion is designated $M^{n+}$, and M is a lanthanide or a transition metal which is iron, manganese, chromium, cobalt or nickel, and n is an integer that is 2 or greater.

88. The device of claim 87, wherein M is a lanthanide and the lanthanide is gadolinium.

89. The method of claim 84, wherein the chelate is selected from the group consisting of diethylenetriaminepentaacetic acid (DTPA), 1,4,7,10-tetracyclododecane-N,N',N",N'"-tetraacetic acid (DOTA) and 1,4,8,11-tetraazacyclotradecane-N,N',N",N'"-tetraacetic acid (TETA), diethylenetriaminepentaacetic acid-N,N'-bis(methylamide) (DTPA-BMA), diethylenetriaminepentaacetic acid-N,N'-bis(methoxyethylamide) (DTPA-BMEA), s-4-(4-ethoxybenzyl)-3,6,9-tris[(carboxylatomethyl)]-3,6,9-triazaundecanedionic acid (EOB-DTPA), benzyloxypropionictetraacetate(BOPTA), (4R)-4-[bis(carboxymethylamino]-3,6,9-triazaundecanedionic acid (MS-325), 1,4,7-tris(carboxymethyl)-10-(2'-hydroxypropyl)-1,4,7,10-tetraazacyclododecane (HP-DO3 A), and DO3A-butrol.

90. The method of claim 84, wherein the hydrogel is collagen, gelatin, hyaluronate, fibrin, alginate, agarose, chitosan, poly(acrylic acid), poly(acrylamide), poly(2-hydroxyethyl methacrylate), poly(N-isopropylacrylamide), poly(ethylene glycol)/poly(ethylene oxide), poly(ethylene oxide)-block-poly(lactic acid), poly(vinyl alcohol), polyphosphazenes, polypeptides or a combination thereof.

91. The method of claim 83, wherein the polymer chain is not covalently linked to the medical device.

92. The method of claim 91, wherein the paramagnetic-metal ion is designated as $M^{n+}$, and M is a lanthanide or a transition metal which is iron, manganese, chromium, cobalt or nickel, and n is an integer that is 2 or greater.

93. The method of claim 92, wherein M is a lanthanide and the lanthanide is gadolinium.

94. The method of claim 91, wherein the chelate is selected from the group consisting of diethylenetriaminepentaacetic acid (DTPA), 1,4,7,10-tetracyclododecane-N,N',N",N'"-tetraacetic acid (DOTA) and 1,4,8,11-tetraazacyclotradecane-N,N',N",N'"-tetraacetic acid (TETA), diethylenetriaminepentaacetic acid-N,N'-bis(methylamide) (DTPA-BMA), diethylenetriaminepentaacetic acid-N,N'-bis(methoxyethylamide) (DTPA-BMEA), s-4-(4-ethoxybenzyl)-3,6,9-tris[(carboxylatomethyl)]-3,6,9-triazaundecanedionic acid (EOB-DTPA), benzyloxypropionictetraacetate(BOPTA), (4R)-4-[bis(carboxymethylamino]-3,6,9-triazaundecanedionic acid (MS-325, 1,4,7-tris(carboxymethyl)-10-(2'-hydroxypropyl)-1,4,7,10-tetraazacyclododecane (HP-DO3A), and DO3A-butrol.

95. The method of claim 91, wherein the hydrogel is collagen, gelatin, hyaluronate, fibrin, alginate, agarose, chitosan, poly(acrylic acid), poly(acrylamide), poly(2-hydroxyethyl methacrylate), poly(N-isopropylacrylamide), poly(ethylene glycol)/poly(ethylene oxide), poly(ethylene oxide)-block-poly(lactic acid), poly(vinyl alcohol), polyphosphazenes, polypeptides or a combination thereof.

96. The method of claim 80, wherein the chain is a second hydrogel.

97. The method of claim 96, wherein the first hydrogel and the second hydrogel are selected from the group consisting of collagen, gelatin, hyaluronate, fibrin, alginate, agarose, chitosan, poly(acrylic acid), poly(acrylamide), poly(2-hydroxyethyl methacrylate), poly(N-isopropylacrylamide), poly(ethylene glycol)/poly(ethylene oxide), poly(ethylene oxide)-block-poly(lactic acid), poly(vinyl alcohol), a polyphosphazene, a polypeptide and combinations thereof, and wherein the first hydrogel and the second hydrogel are the same or different.

98. The method of claim 96, wherein the paramagnetic-metal ion is designated as $M^{n+}$, and M is a lanthanide or a transition metal which is iron, manganese, chromium, cobalt or nickel, and n is an integer that is 2 or greater.

99. The method of claim 98, wherein M is a lanthanide and the lanthanide is gadolinium.

100. The method of claim 94, wherein the chelate is selected from the group consisting of diethylenetriaminepentaacetic acid (DTPA), 1,4,7,10-tetracyclododecane-N,N',N",N'"-tetraacetic acid (DOTA) and 1,4,8,11-tetraazacyclotradecane-N,N',N",N'"-tetraacetic acid (TETA), diethylenetriaminepentaacetic acid-N,N'-bis(methylamide) (DTPA-BMA), diethylenetriaminepentaacetic acid-N,N'-bis(methoxyethylamide) (DTPA-BMEA), s-4-(4-ethoxybenzyl)-3,6,9-tris[(carboxylatomethyl)]-3,6,9-triazaundecanedionic acid (EOB-DTPA), benzyloxypropionictetraacetate(BOPTA), (4R)-4-[bis(carboxymethylamino]-3,6,9-triazaundecanedionic acid (MS-325), 1,4,7-tris(carboxymethyl)-10-(2'-hydroxypropyl)-1,4,7,10-tetraazacyclododecane (HP-DO3A), and DO3A-butrol.

101. The method of claim 80, wherein the chain and the hydrogel are cross-linked using a cross-linker.

102. The method of claim 101, wherein the cross-linker is glutaraldehyde.

* * * * *